(12) United States Patent
Kato et al.

(10) Patent No.: US 11,261,394 B2
(45) Date of Patent: Mar. 1, 2022

(54) FLUORINE-CONTAINING ETHER COMPOUND, LUBRICANT FOR MAGNETIC RECORDING MEDIA, AND MAGNETIC RECORDING MEDIUM

(71) Applicant: SHOWA DENKO K.K., Tokyo (JP)

(72) Inventors: Tsuyoshi Kato, Ichihara (JP); Daisuke Yagyu, Ichihara (JP); Naoya Fukumoto, Ichihara (JP); Masaki Nanko, Ichihara (JP); Masumi Kuritani, Tokyo (JP); Katsumi Murofushi, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 79 days.

(21) Appl. No.: 16/644,586

(22) PCT Filed: Aug. 23, 2018

(86) PCT No.: PCT/JP2018/031161
§ 371 (c)(1),
(2) Date: Mar. 5, 2020

(87) PCT Pub. No.: WO2019/054148
PCT Pub. Date: Mar. 21, 2019

(65) Prior Publication Data
US 2021/0062102 A1    Mar. 4, 2021

(30) Foreign Application Priority Data
Sep. 13, 2017    (JP) .............................. JP2017-176030

(51) Int. Cl.
C10M 105/54    (2006.01)
G11B 5/73    (2006.01)
(Continued)

(52) U.S. Cl.
CPC ........... C10M 105/54 (2013.01); C07C 43/23 (2013.01); C07D 333/16 (2013.01);
(Continued)

(58) Field of Classification Search
CPC .......... C10N 2030/06; C10N 2050/025; C10N 2040/14; C10N 2040/18; C10N 2050/023;
(Continued)

(56) References Cited

U.S. PATENT DOCUMENTS 4,526,833 A * 7/1985 Burguette ............ C09D 171/02
428/336
2010/0233513 A1    9/2010 Imai et al.
(Continued)

FOREIGN PATENT DOCUMENTS

JP    H1160720 A  *  3/1999
JP    2009-266360 A    11/2009
(Continued)

OTHER PUBLICATIONS

International Search Report for PCT/JP2018/031161, dated Nov. 27, 2018 (PCT/ISA/210).

*Primary Examiner* — Vishal V Vasisth
(74) *Attorney, Agent, or Firm* — Sughrue Mion, PLLC

(57) ABSTRACT

A fluorine-containing ether compound represented by $R^1$—$R^2$—$CH_2$—$R^3$—$CH_2$—$R^4$—$R^5$ is provided. ($R^3$ is a perfluoropolyether chain; $R^1$ and $R^5$ are each independently any one of an alkyl group that may have a substituent, an organic group having at least one double bond or at least one triple bond, and a hydrogen atom; and —$R^2$—$CH_2$—$R^3$— is represented by Formula (2), and $R^3$—$CH_2$—$R^4$— is represented by Formula (3))

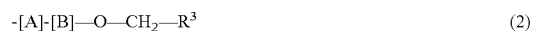

-[A]-[B]—O—$CH_2$—$R^3$    (2)

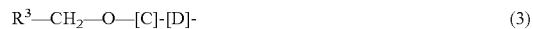

$R^3$—$CH_2$—O—[C]-[D]-    (3)

([A] is represented by Formula (4), [B] is represented by Formula (5), [C] is represented by Formula (6), [D] is represented by Formula (7), and in the formula, a and b are
(Continued)

integers of 0 to 2, c is an integer of 2 to 5, d and f are integers of 0 to 2, and e is an integer of 2 to 5, and at least one of b and d in the formula is 1 or more)

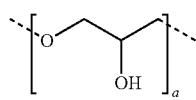

(4)

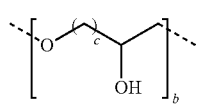

(5)

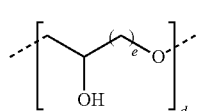

(6)

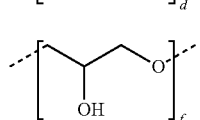

(7)

8 Claims, 1 Drawing Sheet

(51) Int. Cl.
*C07C 43/23* (2006.01)
*C07D 333/16* (2006.01)
*C10N 40/18* (2006.01)

(52) U.S. Cl.
CPC .. *G11B 5/73911* (2019.05); *C10M 2211/0425* (2013.01); *C10N 2040/18* (2013.01)

(58) Field of Classification Search
CPC .............. C10M 147/00; C10M 107/38; C10M 107/24; C10M 107/40; C10M 107/46; C10M 2221/04; C10M 2217/06; C10M 2213/043; C10M 2213/04; C10M 2209/10; C10M 2213/0606; C08G 65/331; G11B 5/7257; G11B 5/7266; G11B 5/725; C07D 231/12; C07D 333/16; C07D 277/24
See application file for complete search history.

(56) References Cited

U.S. PATENT DOCUMENTS

| 2010/0261039 A1 | 10/2010 | Itoh et al. |
| 2012/0225217 A1 | 9/2012 | Itoh et al. |
| 2013/0209837 A1 | 8/2013 | Sagata et al. |
| 2017/0260472 A1 | 9/2017 | Sagata et al. |

FOREIGN PATENT DOCUMENTS

| JP | 2010-143855 A | 7/2010 |
| JP | 4632144 B2 | 2/2011 |
| JP | 2012-009090 A | 1/2012 |
| JP | 2013-163667 A | 8/2013 |
| JP | 5465454 B2 | 4/2014 |
| JP | 5909837 B2 | 4/2016 |
| WO | 2009/035075 A1 | 3/2009 |
| WO | 2016/084781 A1 | 6/2016 |
| WO | 2017/145995 A1 | 8/2017 |

\* cited by examiner

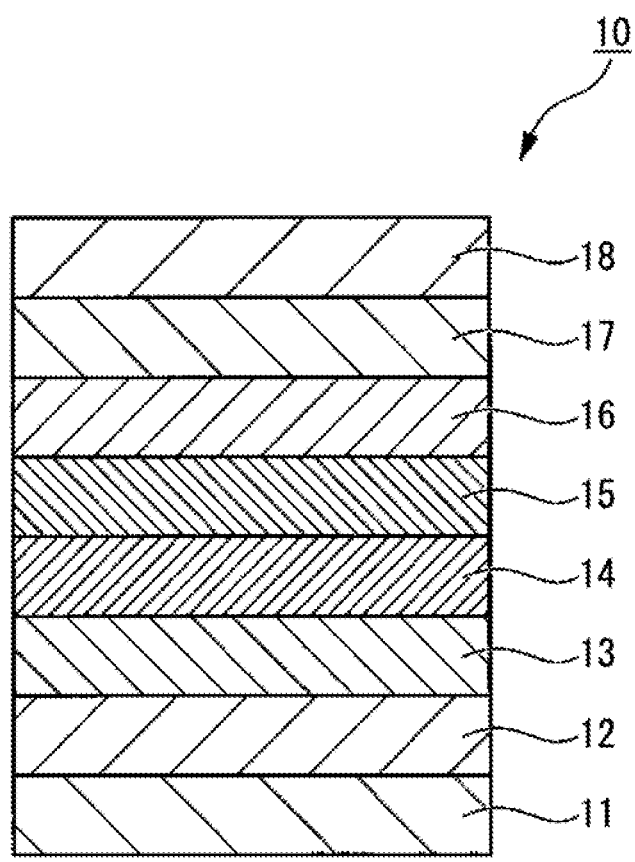

FLUORINE-CONTAINING ETHER COMPOUND, LUBRICANT FOR MAGNETIC RECORDING MEDIA, AND MAGNETIC RECORDING MEDIUM

CROSS REFERENCE TO RELATED APPLICATIONS

This application is a National Stage of International Application No. PCT/JP2018/031161 filed Aug. 23, 2018, claiming priority based on Japanese Patent Application No. 2017-176030, filed Sep. 13, 2017.

TECHNICAL FIELD

The present invention relates to a fluorine-containing ether compound suitable for a use as a lubricant for magnetic recording media, and a lubricant for magnetic recording media and a magnetic recording medium which includes the same.

Priority is claimed on Japanese Patent Application No. 2017-176030, filed on Sep. 13, 2017, the content of which is incorporated herein by reference.

BACKGROUND ART

In order to improve the recording density of a magnetic recording and reproducing apparatus, development of a magnetic recording medium suitable for high recording density is in progress.

In the related art, a magnetic recording medium in which a recording layer is formed on a substrate and a protective layer made of carbon is formed on the recording layer is known. The protective layer protects information recorded in the recording layer and enhances slidability of a magnetic head. However, durability of the magnetic recording medium cannot be sufficiently obtained, simply by providing the protective layer on the recording layer. Therefore, in general, a lubricating layer is formed by applying a lubricant to a surface of the protective layer.

As a lubricant used when forming the lubricating layer for the magnetic recording medium, for example, a lubricant is proposed including a compound having a polar group such as a hydroxyl group at an end of a fluorine polymer having a repeating structure containing $CF_2$ (for example, see Patent Documents 1 to 3).

For example, Patent Document 1 discloses a compound including a substituent having a plurality of hydroxyl groups at both end parts, in which a shortest distance between the hydroxyl groups is 3 atoms or more. In addition, Patent Document 2 discloses a fluoropolyether compound having an aromatic group at one end and a hydroxyl group at the other end. In addition, Patent Document 3 discloses a compound including a perfluoropolyether main chain, and an aromatic group and a hydroxyl group at an end of a molecule, in which the aromatic group and the hydroxyl group are bonded to different carbon atoms.

CITATION LIST

Patent Documents

Patent Document 1: Japanese Patent No. 4632144
Patent Document 2: Japanese Patent No. 5909837
Patent Document 3: Japanese Patent No. 5465454

DISCLOSURE OF INVENTION

Technical Problem

In a magnetic recording and reproducing apparatus, the flying height of a magnetic head needs to be further reduced. Therefore, the thickness of a lubricating layer in a magnetic recording medium needs to be made thinner.

However, in general, when the thickness of the lubricating layer is reduced, coatability of the lubricating layer tends to decrease and wear resistance of the magnetic recording medium tends to decrease.

The present invention was made in view of the above circumstances, and an object thereof is to provide a fluorine-containing ether compound which can be suitably used as a material of a lubricant for magnetic recording media, and which can form a lubricating layer having excellent wear resistance, even when the thickness is reduced.

In addition, another object of the present invention is to provide a lubricant for magnetic recording media including the fluorine-containing ether compound of the present invention.

In addition, still another object of the present invention is to provide a magnetic recording medium which includes a lubricating layer including the fluorine-containing ether compound of the present invention and has excellent reliability and durability.

Solution to Problem

The present inventors have intensively studied to achieve the above objects.

As a result, it was found that a fluorine-containing ether compound including linking groups each having a specific structure, in which an ether bond (—O—), a methylene group (—$CH_2$—), and a methylene group in which one hydrogen atom is substituted with a hydroxyl group (—CH(OH)—) are combined, between a perfluoropolyether chain and both end groups, respectively, may be used, and the present invention was conceived.

That is, the present invention relates to the following aspects.

[1] A fluorine-containing ether compound represented by Formula (1).

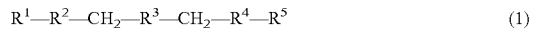

(In Formula (1), $R^3$ is a perfluoropolyether chain, IV is an end group bonded to $R^2$, $R^5$ is an end group bonded to $R^4$, IV and $R^5$ are each independently any one of an alkyl group that may have a substituent, an organic group having at least one double bond or at least one triple bond, and a hydrogen atom, —$R^2$—$CH_2$—$R^3$ is represented by Formula (2), and $R^3$—$CH_2$—$R^4$— is represented by Formula (3))

(In Formula (2), [A] is represented by Formula (4), [B] is represented by Formula (5), and [A] and [B] in Formula (2) may be interchanged)

(In Formula (3), [C] is represented by Formula (6), [D] is represented by Formula (7), and [C] and [D] in Formula (3) may be interchanged)

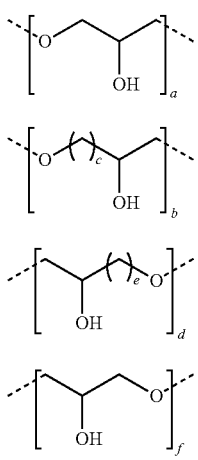

(a in Formula (4) and b in Formula (5) are integers of 0 to 2, c in Formula (5) is an integer of 2 to 5, and d in Formula (6) and f in Formula (7) are an integer of 0 to 2, e in Formula (6) is an integer of 2 to 5, and at least one of b in Formula (5) and d in Formula (6) is 1 or more)

[2] The fluorine-containing ether compound according to [1], in which the alkyl group that may have a substituent is an alkyl group having 1 to 6 carbon atoms, wherein the alkyl group includes a hydroxyl group or a cyano group.

[3] The fluorine-containing ether compound according to [1] or [2], in which the organic group having at least one double bond or at least one triple bond is any one of a group containing an aromatic ring, a group containing a heterocyclic ring, an alkenyl group, and an alkynyl group.

[4] The fluorine-containing ether compound according to any one of [1] to [3], in which $R^3$ in Formula (1) is represented by any one of Formulas (8) to (10).

$$—CF_2O—(CF_2CF_2O)_m—(CF_2O)_n—CF_2— \qquad (8)$$

(m and n in Formula (8) represent average polymerization degrees, and each represent 0 to 30, with a proviso that m or n is 0.1 or more)

$$—CF(CF_3)—(OCF(CF_3)CF_2)_y—OCF(CF_3)— \qquad (9)$$

(y in Formula (9) represents an average degree of polymerization and represents 0.1 to 30)

$$—CF_2CF_2O—(CF_2CF_2CF_2O)_z—CF_2CF_2— \qquad (10)$$

(In Formula (10), z represents an average degree of polymerization and represents 0.1 to 30)

[5] The fluorine-containing ether compound according to any one of [1] to [4], in which a number-average molecular weight is in a range of 500 to 10000.

[6] A lubricant for magnetic recording media including the fluorine-containing ether compound according to any one of [1] to [5].

[7] A magnetic recording medium including: a substrate; and at least a magnetic layer, a protective layer, and a lubricating layer in this order on the substrate, in which the lubricating layer includes the fluorine-containing ether compound according to any one of [1] to [5].

[8] The magnetic recording medium according to [7], in which an average film thickness of the lubricating layer is 0.5 nm to 2 nm.

Advantageous Effects of Invention

The fluorine-containing ether compound of the present invention is suitable as a material of a lubricant for magnetic recording media.

Since the lubricant for magnetic recording media of the present invention includes the fluorine-containing ether compound of the present invention, it is possible to form a lubricating layer in which excellent wear resistance is obtained even when the thickness thereof is reduced.

The magnetic recording medium of the present invention is provided with a lubricating layer having excellent wear resistance, and thus has excellent reliability and durability.

BRIEF DESCRIPTION OF DRAWINGS

FIG. 1 is a schematic sectional view showing a magnetic recording medium according to an embodiment of the present invention.

BEST MODE FOR CARRYING OUT THE INVENTION

Hereinafter, a fluorine-containing ether compound, a lubricant for magnetic recording media (hereinafter sometimes abbreviated as a "lubricant"), and a magnetic recording medium of the present invention will be described in detail. The present invention is not limited to only the embodiments shown below. For example, the present invention is not limited to only the following examples, and addition, omission, substitution, or a change in the number, the amount, a ratio, a material, a configuration, and the like can be made within the scope not departing from the gist of the present invention.

[Fluorine-Containing Ether Compound]

The fluorine-containing ether compound of the present embodiment is represented by Formula (1).

$$R^1—R^2—CH_2—R^3—CH_2—R^4—R^5 \qquad (1)$$

(In Formula (1), $R^3$ is a perfluoropolyether chain. $R^1$ is an end group bonded to $R^2$. $R^5$ is an end group bonded to $R^4$. $R^1$ and $R^5$ are each independently any one of an alkyl group that may have a substituent, an organic group having at least one double bond or at least one triple bond, and a hydrogen atom. $—R^2—CH_2—R^3$ is represented by Formula (2), and $R^3—CH_2—R^4—$ is represented by Formula (3).)

$$\text{-[A]-[B]—O—CH}_2—R^3 \qquad (2)$$

$$R^3—CH_2—O—[C]\text{-[D]-} \qquad (3)$$

(In Formula (2), [A] is represented by Formula (4), [B] is represented by Formula (5), and [A] and [B] in Formula (2) may be interchanged)

(In Formula (3), [C] is represented by Formula (6), [D] is represented by Formula (7), and [C] and [D] in Formula (3) may be interchanged)

(4)

(5)

(6)

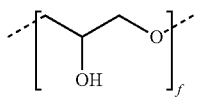

(a in Formula (4) and b in Formula (5) are integers of 0 to 2, c in Formula (5) is an integer of 2 to 5, and d in Formula (6) and f in Formula (7) are an integer of 0 to 2, e in Formula (6) is an integer of 2 to 5, and at least one of b in Formula (5) and d in Formula (6) is 1 or more)

Here, in a case where a lubricating layer is formed on a protective layer of the magnetic recording medium by using a lubricant including the fluorine-containing ether compound of the present embodiment, the reason why excellent wear resistance is obtained even when the thickness is reduced will be described.

The fluorine-containing ether compound of the present embodiment includes a perfluoropolyether chain (hereinafter sometimes abbreviated as a "PFPE chain") represented by $R^3$ as shown in Formula (1). In the lubricating layer including the fluorine-containing ether compound of the present embodiment, the PFPE chain covers a surface of the protective layer and imparts lubricity to the lubricating layer to reduce frictional force between a magnetic head and the protective layer.

In addition, in Formula (1), $-R^2-CH_2-R^3$ is represented by Formula (2), and $R^3-CH_2-R^4-$ is represented by Formula (3). In Formula (2), [A] is represented by Formula (4), [B] is represented by Formula (5). In Formula (3), [C] is represented by Formula (6), and [D] is represented by Formula (7). At least one of b in Formula (5) and d in Formula (6) is 1 or more.

Therefore, the fluorine-containing ether compound represented by Formula (1) includes one or more hydroxyl groups in total in $R^2$ and $R^4$. In the lubricating layer including the fluorine-containing ether compound of the present embodiment, the hydroxyl group included in $R^2$ or $R^4$ brings the fluorine-containing ether compound and the protective layer into close contact with each other to improve wear resistance. Accordingly, it is presumed that, with the lubricant including the fluorine-containing ether compound, a lubricating layer having excellent wear resistance can be formed even when the thickness is reduced.

In addition, in the fluorine-containing ether compound of the present embodiment, an excellent effect is obtained compared to other compounds. For example, compared to a compound in which, in Formula (1), $-R^2-CH_2-R^3$ is represented by Formula (2) and $R^3-CH_2-R^4-$ is represented by Formula (3), in Formula (2), [A] is represented by Formula (4) and [B] is represented by Formula (5), in Formula (3), [C] is represented by Formula (6) and [D] is represented by Formula (7), b in Formula (5) and d in Formula (6) are 0 (zero), and at least one of a in Formula (4) and f in Formula (7) is 1 or more (in other words, [B] and [C] are not included and at least one of [A] and [D] is included), the fluorine-containing ether compound of the present embodiment can obtain the following effects.

That is, in the fluorine-containing ether compound of the present embodiment, at least one of b in Formula (5) and d in Formula (6) is 1 or more (in other words, at least one of [B] and [C] is included). Therefore, compared to a compound in which b and d are 0 (zero) and at least one of a and f is 1 or more, the distance between the hydroxyl group closest to $R^3$ in $R^2$ ($R^4$) and $R^1$ ($R^5$) is long. Therefore, it is presumed that the lubricating layer including the fluorine-containing ether compound of the present embodiment has small interaction (for example, hydrogen bonding) in the fluorine-containing ether compound, and affinity of $R^1$ ($R^5$) and a hydroxyl group in the fluorine-containing ether compound with the protective layer is enhanced, and as a result, favorable wear resistance is obtained.

$R^2$ is a divalent linking group, and $-R^2-CH_2-R^3$ is represented by Formula (2). In Formula (2), [A] is represented by Formula (4), [B] is represented by Formula (5). a in Formula (4) and b in Formula (5) are integers of 0 to 2, and c in Formula (5) is an integer of 2 to 5.

In order to further improve adhesion between the fluorine-containing ether compound and the protective layer in the lubricating layer including the fluorine-containing ether compound, it is preferable that at least one of a in Formula (4) and b in Formula (5) be 1 or more (that is, in Formula (2), at least one of [A] and [B] is included). The sum of a in Formula (4) and b in Formula (5) is 4 or less, and preferably 2 or less. When the sum of a in Formula (4) and b in Formula (5) is 2 or less, it is possible to prevent pickup, which is adherence to a magnetic head as a foreign substance (smear) and tends to be caused when polarity of the fluorine-containing ether compound is too high, from occurring, which is preferable.

c in Formula (5) is an integer of 2 to 5, preferably an integer of 2 to 4, and most preferably 2. When c in Formula (5) is an integer of 2 to 5, the distance between the hydroxyl group in Formula (5) and $R^1$ and/or the distance between the hydroxyl groups in Formula (5) becomes appropriate, which is preferable.

It is preferable that $-R^2-$ in Formula (2) be any one of structures represented by Formulas (11) to (13). In the structures represented by Formulas (11) to (13), $R^1$ is bonded to the leftmost oxygen atom. In Formulas (11) to (13), a is a numerical value of a in Formula (4), and b and c are numerical values of b and c in Formula (5), respectively.

In the fluorine-containing ether compound of the present embodiment, $-R^2-$ in Formula (2) can be appropriately selected according to a performance required for the lubricant including the fluorine-containing ether compound.

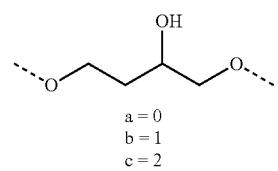

a = 0
b = 1
c = 2

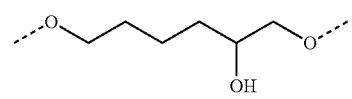

a = 0
b = 1
c = 4

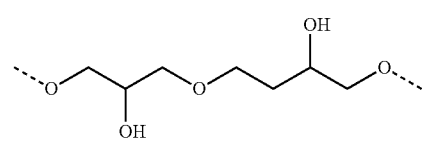

a = 1
b = 1
c = 2

$R^4$ is a divalent linking group, and $R^3$—$CH_2$—$R^4$— is represented by Formula (3). In Formula (3), [C] is represented by Formula (6), and [D] is represented by Formula (7). d in Formula (6) and f in Formula (7) are integers of 0 to 2, and e in Formula (6) is an integer of 2 to 5.

In the lubricating layer including the fluorine-containing ether compound, in order to further improve adhesion between the fluorine-containing ether compound and the protective layer, it is preferable that at least one of d in Formula (6) and f in Formula (7) be 1 or more (that is, in Formula (3), at least one of [C] and [D] is included). The sum of d in Formula (6) and f in Formula (7) is 4 or less, and preferably 2 or less. When the sum of d in Formula (6) and f in Formula (7) is 2 or less, it is possible to prevent pickup, which is adherence to a magnetic head as a foreign substance (smear) and tends to be caused when polarity of the fluorine-containing ether compound is too high, from occurring, which is preferable.

e in Formula (6) is an integer of 2 to 5, preferably an integer of 2 to 4, and most preferably 2. When e in Formula (6) is an integer of 2 to 5, the distance between the hydroxyl group in Formula (6) and $R^5$ and/or the distance between the hydroxyl groups in Formula (6) becomes appropriate, which is preferable.

It is preferable that —$R^4$— in Formula (3) be any one of structures represented by Formulas (14) to (17). In the structures represented by Formulas (14) to (17), $R^5$ is bonded to the rightmost oxygen atom. In Formulas (14) to (17), d and e are numerical values of d and e in Formula (6), and f is a numerical value of f in Formula (7).

In the fluorine-containing ether compound of the present embodiment, —$R^4$— in Formula (3) can be appropriately selected according to a performance required for the lubricant including the fluorine-containing ether compound.

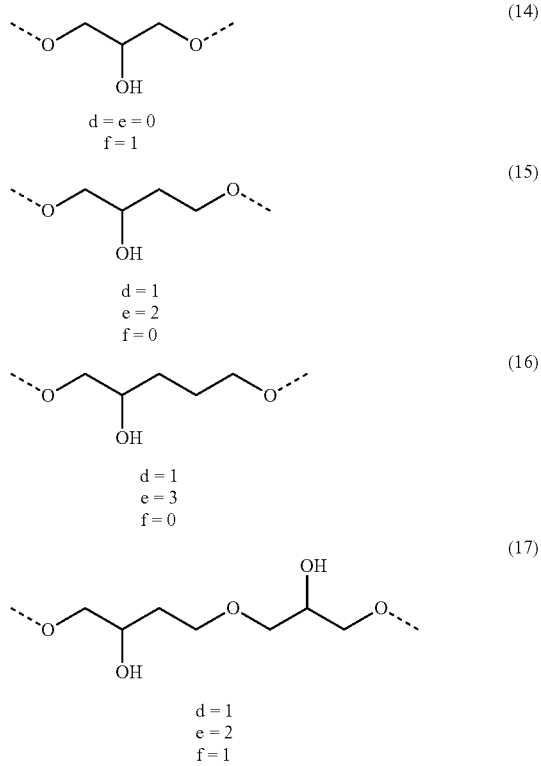

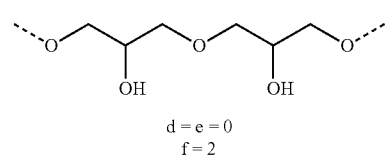

In the fluorine-containing ether compound of the present embodiment, at least one of b in Formula (5) and d in Formula (6) is 1 or more. Therefore, in a case where a in Formula (4) and f in Formula (7) are both 0 (zero), and either b in Formula (5) or d in Formula (6) is 0 (zero) (that is, [A] and [D] are not included and at least one of [B] and [C] is included), the fluorine-containing ether compound having only one of $R^2$ or $R^4$ in Formula (1) is obtained.

In the present embodiment, it is preferable that at least one of b in Formula (5) and d in Formula (6) be 1 or more, and the sum of a in Formula (4) and b in Formula (5) and the sum of d in Formula (6) and f in Formula (7) are 1 or more.

In addition, in the fluorine-containing ether compound represented by Formula (1), in a case where $R^4$ includes only [C] and $R^5$ is a hydrogen atom, it is preferable that $R^2$ include [B] to obtain better wear resistance. In addition, in the fluorine-containing ether compound represented by Formula (1), in a case where $R^2$ includes only [B] and $R^1$ is a hydrogen atom, it is preferable that $R^4$ include [C] to obtain better wear resistance.

In the fluorine-containing ether compound of the present embodiment, the sum of the number of hydroxyl groups (—OH) included in $R^2$ and the number of hydroxyl groups included in $R^4$ is 1 or more, and preferably 2 or more, and it is more preferable that $R^2$ and $R^4$ each includes one or more hydroxyl groups. When $R^2$ and $R^4$ each includes one or more hydroxyl groups, in the lubricating layer including the fluorine-containing ether compound, the adhesion between the fluorine-containing ether compound and the protective layer becomes better, which is preferable.

The sum of the number of hydroxyl groups included in $R^2$ and the number of hydroxyl groups included in $R^4$ is 8 or less, preferably 6 or less, and more preferably 4 or less. When the sum of the number of hydroxyl groups included in $R^2$ and the number of hydroxyl groups included in $R^4$ is 8 or less, it is possible to prevent pickup, which is adherence to a magnetic head as a foreign substance (smear) and tends to be caused when polarity of the fluorine-containing ether compound is too high, from occurring, which is more preferable.

In the fluorine-containing ether compound of the present embodiment represented by Formula (1), $R^1$ is an end group bonded to $R^2$, and $R^5$ is an end group bonded to $R^4$.

$R^1$ and $R^5$ are each independently any one of an alkyl group that may have a substituent, an organic group having at least one double bond or at least one triple bond, and a hydrogen atom. The alkyl group that may have a substituent and the organic group having at least one double bond or at least one triple bond may contain any one of an oxygen atom, a sulfur atom and a nitrogen atom.

In the alkyl group that may have a substituent, the alkyl group is preferably an alkyl group having 1 to 8 carbon atoms, and more preferably an alkyl group having 1 to 6 carbon atoms. Specific examples thereof include a methyl group, an ethyl group, a propyl group, a butyl group, a pentyl group, a hexyl group, a heptyl group, and an octyl group, which may be linear or branched.

Examples of the substituent in the alkyl group that may have a substituent include a halogeno group, an alkoxy group, a hydroxyl group, and a cyano group. In a case where the alkyl group that may have a substituent has these substituents, a fluorine-containing ether compound capable of forming a lubricating layer having more excellent wear resistance is obtained.

Examples of the alkyl group having the halogeno group include a trifluoromethyl group, a perfluoroethyl group, a perfluoropropyl group, a perfluorobutyl group, a perfluoropentyl group, a perfluorohexyl group, an octafluoropentyl group, and a tridecafluorooctyl group.

Examples of the alkyl group having the hydroxyl group as a substituent include an alkyl group represented by Formula (18). When at least one of $R^1$ and $R^5$ is the alkyl group represented by Formula (18), affinity between the lubricating layer including the fluorine-containing ether compound and the protective layer becomes further favorable, which is preferable.

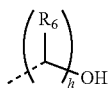 (18)

(In Formula (18), $R_6$ represents an alkyl group having 1 to 4 carbon atoms or a hydrogen atom, and h represents an integer of 1 to 6.)

In Formula (18), $R_6$ is an alkyl group having 1 to 4 carbon atoms or a hydrogen atom and is preferably a hydrogen atom. In a structure represented by Formula (18), the left side is bonded to $R^2$ or $R^4$. In Formula (18), h represents an integer of 1 to 6, and preferably an integer of 1 to 4. When the number of carbon atoms in Formula (18) (the total number of carbon atoms contained in $R_6$ and h) is 1 to 6, a proportion of fluorine atoms in a fluorine-containing ether compound molecule is not low, and therefore, there is no decrease in surface free energy of the whole molecule, which is preferable.

Examples of the alkyl group having the cyano group as a substituent include an alkyl group represented by Formula (19).

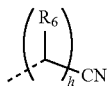 (19)

(In Formula (19), $R_6$ represents an alkyl group having 1 to 4 carbon atoms or a hydrogen atom, and i represents an integer of 1 to 6.)

In Formula (19), $R_6$ is an alkyl group having 1 to 4 carbon atoms or a hydrogen atom and is preferably a hydrogen atom. In a structure represented by Formula (19), the left side is bonded to $R^2$ or $R^4$.

In Formula (19), i represents an integer of 1 to 6, and preferably an integer of 1 to 4. When the number of carbon atoms in Formula (19) (the total number of carbon atoms contained in $R_6$ and i) is 1 to 6, a proportion of fluorine atoms in a fluorine-containing ether compound molecule is not low, and therefore, there is no decrease in surface free energy of the whole molecule, which is preferable.

Examples of the organic group having at least one double bond or at least one triple bond include a group containing an aromatic ring, a group containing a heterocyclic ring, an alkenyl group, and an alkynyl group. Specific examples of the organic group having at least one double bond or at least one triple bond can include a phenyl group, a methoxyphenyl group, a phenyl fluoride group, a naphthyl group, a phenethyl group, a methoxyphenethyl group, a fluorinated phenethyl group, a benzyl group, a methoxybenzyl group, a naphthylmethyl group, a methoxynaphthyl group, a pyrrolyl group, a pyrazolyl group, a methylpyrazolylmethyl group, an imidazolyl group, a furyl group, a furfuryl group, an oxazolyl group, an isoxazolyl group, a thienyl group, a thienylethyl group, a thiazolyl group, a methylthiazolylethyl group, an isothiazolyl group, a pyridyl group, a pyrimidinyl group, a pyridazinyl group, a pyrazinyl group, an indolinyl group, a benzofuranyl group, a benzothienyl group, a benzimidazolyl group, a benzoxazolyl group, a benzothiazolyl group, a benzopyrazolyl group, a benzoisoxazolyl group, a benzoisothiazolyl group, a quinolyl group, an isoquinolyl group, a quinazolinyl group, a quinoxalinyl group, a phthalazinyl group, a cinnolinyl group, a vinyl group, an allyl group, a butenyl group, a propynyl group, a propargyl group, a butynyl group, a methylbutynyl group, a pentynyl group, a methylpentynyl group, and a hexynyl group.

As the organic group having at least one double bond or at least one triple bond, among the above examples, in particular, any one of the phenyl group, the methoxyphenyl group, the thienylethyl group, the butenyl group, the allyl group, the propargyl group, the phenethyl group, the methoxyphenethyl group, and the fluorinated phenethyl group is preferable, and the phenyl group, the thienylethyl group, the allyl group, or the butenyl group is further preferable. In a case where the organic group having at least one double bond or at least one triple bond is any one of the phenyl group, the thienylethyl group, the allyl group, and the butenyl group, a fluorine-containing ether compound capable of forming a lubricating layer having more excellent wear resistance is obtained.

The organic group having at least one double bond or at least one triple bond may have a substituent such as an alkyl group, an alkoxy group, a hydroxyl group, a mercapto group, a carboxyl group, a carbonyl group, an amino group, or a cyano group.

In the fluorine-containing ether compound of the present embodiment represented by Formula (1), $R^3$ is a perfluoropolyether chain (PFPE chain). $R^3$ is not particularly limited, and can be appropriately selected according to a performance or the like required for the lubricant including the fluorine-containing ether compound. Examples of the PFPE chain include a chain based on a perfluoromethylene oxide polymer, a perfluoroethylene oxide polymer, a perfluoro-n-propylene oxide polymer, a perfluoroisopropylene oxide polymer, and a copolymer of these polymers.

Specifically, $R^3$ in Formula (1) is preferably represented by any one of Formulas (8) to (10). An arrangement order of $(CF_2CF_2O)$ and $(CF_2O)$ which are repeating units in Formula (8) is not particularly limited. In Formula (8), any one of a random copolymer, a block copolymer, and an alternating copolymer including monomer units of $(CF_2-CF_2-O)$ and $(CF_2-O)$ may be included.

$$-CF_2O-(CF_2CF_2O)_m-(CF_2O)_n-CF_2- \quad (8)$$

(m and n in Formula (8) represent average polymerization degrees, and each represent 0 to 30, with a proviso that m or n is 0.1 or more.)

$$-CF(CF_3)-(OCF(CF_3)CF_2)_y-OCF(CF_3)- \quad (9)$$

(y in Formula (9) represents an average degree of polymerization and represents 0.1 to 30.)

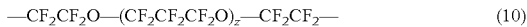
$$—CF_2CF_2O—(CF_2CF_2CF_2O)_z—CF_2CF_2— \quad (10)$$

(In Formula (10), z represents an average degree of polymerization and represents 0.1 to 30.)

When y and z in Formulas (9) and (10) each represent 0.1 to 30, and when m and n in Formula (8) each represent 0 to 30 and m or n represents 0.1 or more, a fluorine-containing ether compound capable of obtaining a lubricating layer having favorable wear resistance is obtained. However, when m, n, y, and z each exceed 30, viscosity of the fluorine-containing ether compound increases, and a lubricant including the compound may be difficult to apply in some cases. Therefore, m, n, y, and z are preferably 30 or less, and more preferably 20 or less.

In a case where $R^3$ in Formula (1) is represented by any one of Formulas (8) to (10), the fluorine-containing ether compound is easily synthesized, which is preferable. In a case where $R^3$ is represented by Formula (8), a raw material is easily available, which is more preferable.

In addition, in a case where $R^3$ is represented by any one of Formulas (8) to (10), a ratio of the number of oxygen atoms (the number of ether bonds (—O—)) to the number of carbon atoms in the perfluoropolyether chain is appropriate. Therefore, a fluorine-containing ether compound having an appropriate rigidity is obtained. Accordingly, the fluorine-containing ether compound applied on the protective layer is less likely to aggregate on the protective layer, and the lubricating layer of which the thickness is thinner can be formed with sufficient coverage. In addition, in a case where $R^3$ is represented by any one of Formulas (8) to (10), a fluorine-containing ether compound capable of obtaining a lubricating layer having favorable wear resistance is obtained.

In the fluorine-containing ether compound represented by Formula (1), $R^1$ and $R^5$ may be the same as or different from each other. When $R^1$ and $R^5$ are the same as each other, easy production is possible, which is preferable.

In addition, in the fluorine-containing ether compound represented by Formula (1), $R^2$ and $R^4$ may be the same as or different from each other. When $R^2$ and $R^4$ are the same as each other, easy production is possible, which is preferable.

Therefore, in the fluorine-containing ether compound represented by Formula (1), when $R^1$ and $R^5$ are the same as each other and $R^2$ and $R^4$ are the same as each other, easier production is possible, which is preferable.

Specifically, it is preferable that the fluorine-containing ether compound represented by Formula (1) be any one of compounds represented by Formulas (A) to (Q). Since repetition numbers m and n in Formulas (A) to (L) and (N) to (Q) and repetition number z in Formula (M) are values showing an average value, the number is not necessarily an integer.

In the compound represented by Formula (A), $R^1$ is a group containing an aromatic ring, $R^2$ includes only [B], $R^3$ is represented by Formula (8), $R^4$ includes only [D], and $R^5$ is a hydrogen atom.

In the compound represented by Formula (B), $R^1$ is a group containing an aromatic ring, $R^2$ includes only [B], $R^3$ is represented by Formula (8), $R^4$ includes only [C], and $R^5$ is a hydrogen atom.

In the compound represented by Formula (C), $R^1$ is a group containing an aromatic ring, $R^2$ includes only [B], $R^3$ is represented by Formula (8), $R^4$ includes only [D], and $R^5$ is an alkyl group having a hydroxyl group at the end.

In the compound represented by Formula (D), $R^1$ is an alkenyl group, $R^2$ includes only [B], $R^3$ is represented by Formula (8), $R^4$ includes only [D], and $R^5$ is a hydrogen atom.

In the compound represented by Formula (E), $R^1$ is an alkenyl group, $R^2$ includes only [B], $R^3$ is represented by Formula (8), $R^4$ includes only [C], and $R^5$ is a hydrogen atom.

In the compound represented by Formula (F), $R^1$ is an alkenyl group, $R^2$ includes only [B], $R^3$ is represented by Formula (8), $R^4$ includes only [D], and $R^5$ is an alkyl group having a hydroxyl group at the end.

In the compound represented by Formula (G), $R^1$ is a group containing a heterocyclic ring, $R^2$ includes only [B], $R^3$ is represented by Formula (8), $R^4$ includes only [D], and $R^5$ is a hydrogen atom.

In the compound represented by Formula (H), $R^1$ is a group containing a heterocyclic ring, $R^2$ includes only [B], $R^3$ is represented by Formula (8), $R^4$ includes only [C], and $R^5$ is a hydrogen atom.

In the compound represented by Formula (I), $R^1$ is a group containing a heterocyclic ring, $R^2$ includes only [B], $R^3$ is represented by Formula (8), $R^4$ includes only [D], and $R^5$ is an alkyl group having a hydroxyl group at the end.

In the compound represented by Formula (J), $R^1$ is an alkenyl group, $R^2$ includes only [B], $R^3$ is represented by Formula (8), $R^4$ includes only [D], and $R^5$ is an alkyl group having a hydroxyl group at the end.

In the compound represented by Formula (K), $R^1$ is an alkenyl group, $R^2$ includes [A] and [B], $R^3$ is represented by Formula (8), $R^4$ includes only [D], and $R^5$ is an alkyl group having a hydroxyl group at the end.

In the compound represented by Formula (L), $R^1$ is an alkenyl group, $R^2$ includes [A] and [B], $R^3$ is represented by Formula (8), $R^4$ includes [C] and [D], and $R^5$ is an alkenyl group. In the compound represented by Formula (L), $R^1$ and $R^5$ are the same, and $R^2$ and $R^4$ are the same.

In the compound represented by Formula (M), $R^1$ is an alkenyl group, $R^2$ includes only [B], $R^3$ is represented by Formula (10), $R^4$ includes only [C], and $R^5$ is an alkyl group having a hydroxyl group at the end.

In the compound represented by Formula (N), $R^1$ is a group containing an aromatic ring, $R^2$ includes only [B], $R^3$ is represented by Formula (8), $R^4$ includes only [C], $R^5$ is a group containing an aromatic ring, $R^1$ and $R^5$ are the same, and $R^2$ and $R^4$ are the same.

In the compound represented by Formula (O), $R^1$ is an alkyl group having a hydroxyl group at the end, $R^2$ includes only [B], $R^3$ is represented by Formula (8), $R^4$ includes only [C], $R^5$ is an alkyl group having a hydroxyl group at the end, $R^1$ and $R^5$ are the same, and $R^2$ and $R^4$ are the same.

In the compound represented by Formula (P), $R^1$ is an alkenyl group, $R^2$ includes [A] and [B], $R^3$ is represented by Formula (8), $R^4$ includes only [D], and $R^5$ is an alkyl group having a cyano group at the end.

In the compound represented by Formula (Q), $R^1$ is an alkenyl group, $R^2$ includes only [B], $R^3$ is represented by Formula (8), $R^4$ includes only [C], and $R^5$ is an alkyl group having a cyano group at the end.

The compounds represented by Formulas (A) to (T) are shown below.

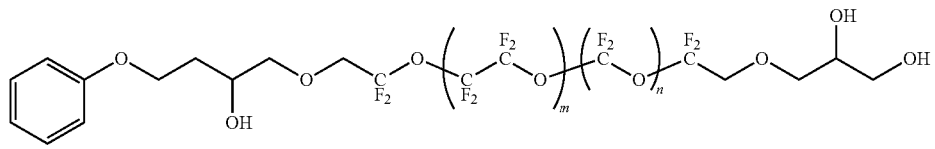

(A)

(In Formula (A), m and n represent average polymerization degrees, m represents 1 to 30, and n represents 0 to 30.)

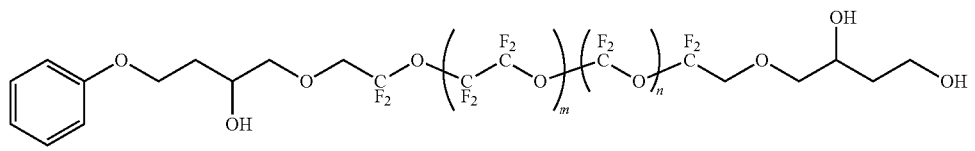

(B)

(In Formula (B), m and n represent average polymerization degrees, m represents 1 to 30, and n represents 0 to 30.)

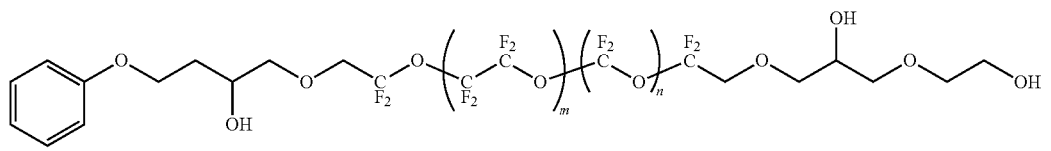

(C)

(In Formula (C), m and n represent average polymerization degrees, m represents 1 to 30, and n represents 0 to 30.)

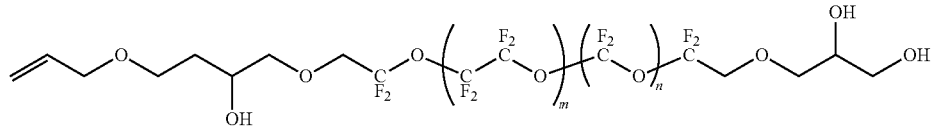

(D)

(In Formula (D), m and n represent average polymerization degrees, m represents 1 to 30, and n represents 0 to 30.)

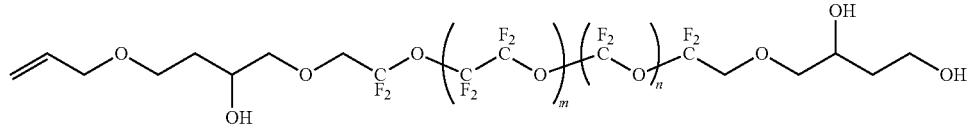

(E)

(In Formula (E), m and n represent average polymerization degrees, m represents 1 to 30, and n represents 0 to 30.)

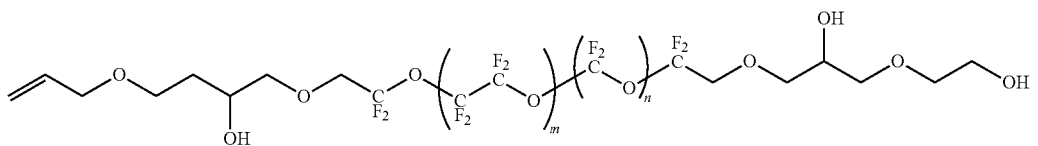

(F)

(In Formula (F), m and n represent average polymerization degrees, m represents 1 to 30, and n represents 0 to 30.)

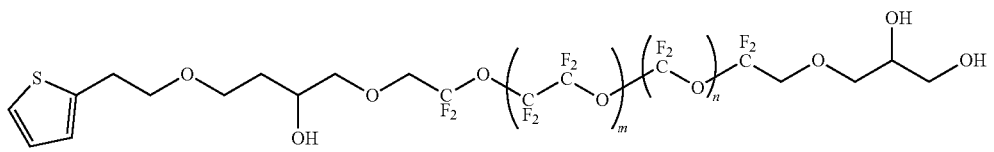

(G)

(In Formula (G), m and n represent average polymerization degrees, m represents 1 to 30, and n represents 0 to 30.)

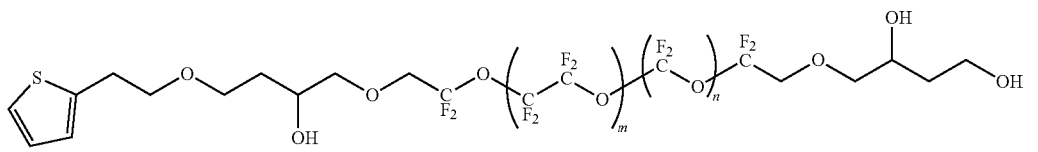

(H)

(In Formula (H), m and n represent average polymerization degrees, m represents 1 to 30, and n represents 0 to 30.)

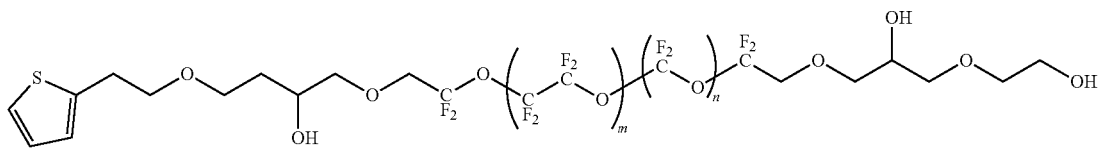

(I)

(In Formula (I), m and n represent average polymerization degrees, m represents 1 to 30, and n represents 0 to 30.)

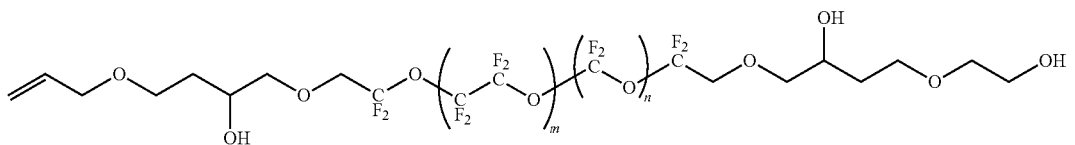

(J)

(In Formula (J), m and n represent average polymerization degrees, m represents 1 to 30, and n represents 0 to 30.)

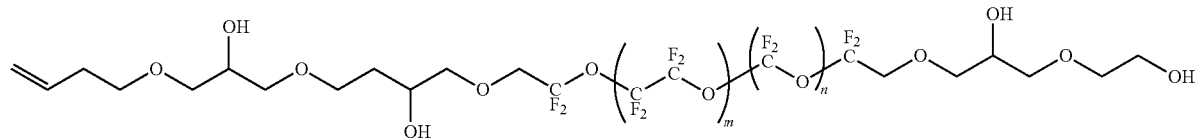

(K)

(In Formula (K), m and n represent average polymerization degrees, m represents 1 to 30, and n represents 0 to 30.)

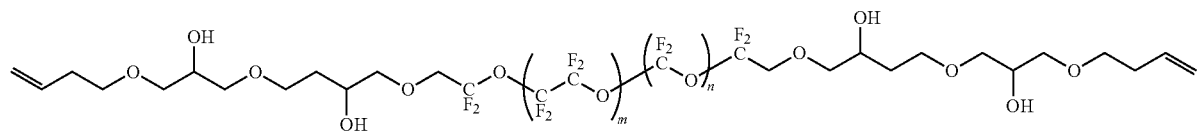

(L)

(In Formula (L), m and n represent average polymerization degrees, m represents 1 to 30, and n represents 0 to 30.)

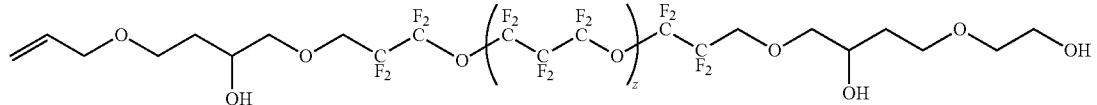

(M)

(In Formula (M), z represents an average polymerization degree, and z represents 1 to 30.)

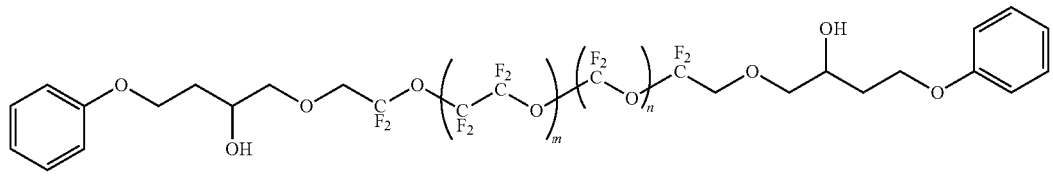

(N)

(In Formula (N), m and n represent average polymerization degrees, m represents 1 to 30, and n represents 0 to 30.)

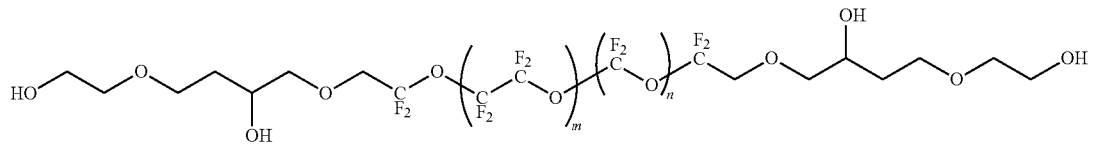

(O)

(In Formula (O), m and n represent average polymerization degrees, m represents 1 to 30, and n represents 0 to 30.)

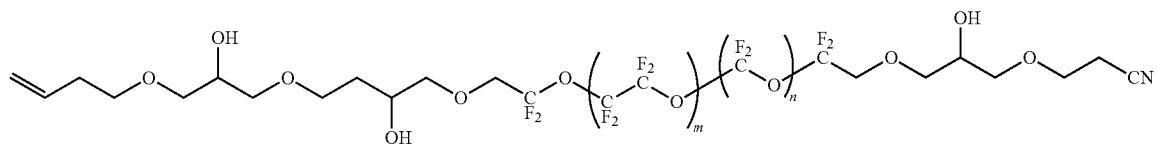

(P)

(In Formula (P), m and n represent average polymerization degrees, m represents 1 to 30, and n represents 0 to 30.)

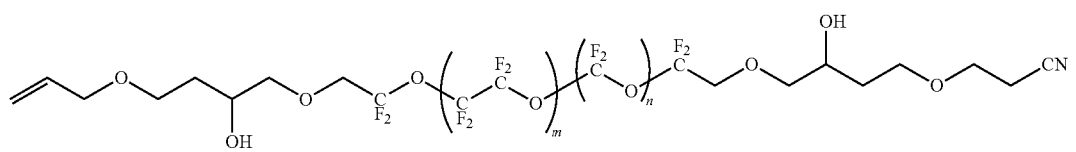

(Q)

(In Formula (Q), m and n represent average polymerization degrees, m represents 1 to 30, and n represents 0 to 30.)

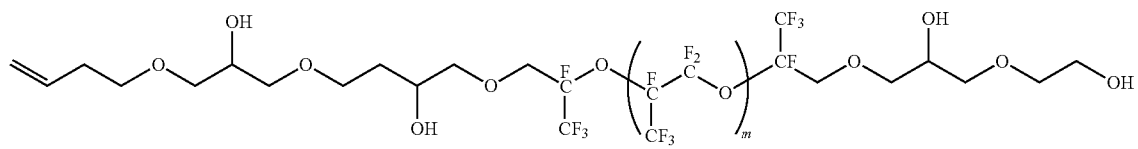

(R)

(In Formula (R), m represents an average polymerization degree, and m represents 1 to 30.)

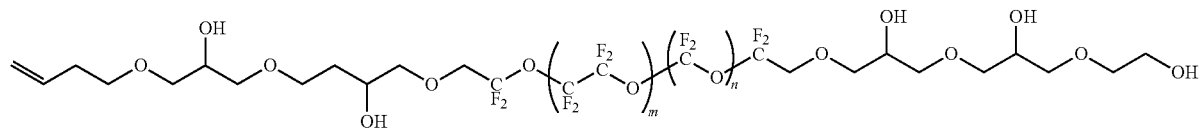

(S)

(In Formula (S), m and n represent average polymerization degrees, m represents 1 to 30, and n represents 0 to 30.)

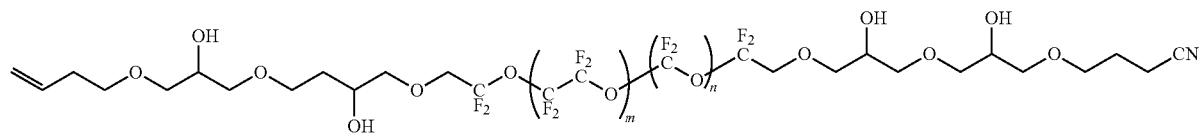

(T)

(In Formula (T), m and n represent average polymerization degrees, m represents 1 to 30, and n represents 0 to 30.)

When the compound represented by Formula (1) is any one of the compounds represented by the Formulas (A) to (T), a raw material is easily available, and it is possible to form a lubricating layer in which excellent wear resistance is obtained even when the thickness thereof is reduced, which is preferable.

In the fluorine-containing ether compound of the present embodiment, a number-average molecular weight (Mn) is preferably in a range of 500 to 10000. When the number-average molecular weight is 500 or more, the lubricant including the fluorine-containing ether compound of the present embodiment is less likely to evaporate, and it is possible to prevent the lubricant from evaporating and transferring to a magnetic head. The number-average molecular weight of the fluorine-containing ether compound is more preferably 1000 or more. In addition, when the number-average molecular weight is 10000 or less, the viscosity of the fluorine-containing ether compound is appropriate, and when applying a lubricant including the compound, a lubricating layer having a reduced thickness can be easily formed. The number-average molecular weight of the fluorine-containing ether compound is preferably 3000 or less, from the viewpoint that viscosity for easy handling is obtained in a case of being applied to a lubricant.

The number-average molecular weight (Mn) of the fluorine-containing ether compound is a value measured by $^1$H-NMR and $^{19}$F-NMR using AVANCE III 400 manufactured by Bruker Biospin. In measurement of nuclear magnetic resonance (NMR), a sample was diluted in a single or mixed solvent such as hexafluorobenzene, d-acetone, and d-tetrahydrofuran to be used for the measurement. For the standard of $^{19}$F-NMR chemical shift, the peak of hexafluorobenzene was set to −164.7 ppm. For the standard of $^1$H-NMR chemical shift, the peak of acetone was set to 2.2 ppm.

"Production Method"

A production method of the fluorine-containing ether compound of the present embodiment is not particularly limited, and the fluorine-containing ether compound can be produced using a known production method of the related art. The fluorine-containing ether compound of the present embodiment can be produced, for example, using the following production method.

First, a fluorine-based compound including hydroxymethyl groups (—CH$_2$OH) respectively at both ends of a perfluoropolyether chain corresponding to R$^3$ in Formula (1) is prepared.

Next, a hydroxyl group of the hydroxymethyl group at one end of the fluorine-based compound is substituted with a group shown as R$^1$—R$^2$— in Formula (1) (first reaction). Thereafter, the hydroxyl group of the hydroxymethyl group at the other end is substituted with an end group shown as —R$^4$—R$^5$ in Formula (1) (second reaction).

The first reaction and the second reaction can be performed using a method known in the related art, and can be appropriately determined according to types of R$^1$, R$^2$, R$^4$, and R$^5$ in Formula (1). In addition, either the first reaction or the second reaction may be performed first. In a case where R$^1$ and R$^5$ are the same and R$^2$ and R$^4$ are the same, the first reaction and the second reaction may be performed simultaneously.

A compound represented by Formula (1) is obtained by using the method as above.

In the present embodiment, it is preferable to use an epoxy compound in order to produce a fluorine-containing ether compound in which R$^2$ is represented by Formula (2) and R$^4$ is represented by Formula (3). The epoxy compound can be purchased commercially, and can also be synthesized using an alcohol having a structure corresponding to the end group represented by R$^1$ or R$^5$ of a fluorine-containing ether compound to be produced and any one selected from epichlorohydrin, epibromohydrin, or 2-bromoethyloxirane. In addition, the epoxy compound may be synthesized by oxidizing an unsaturated bond.

The fluorine-containing ether compound of the present embodiment is a compound represented by Formula (1). Therefore, when the lubricating layer is formed on the protective layer using a lubricant including the compound, the surface of the protective layer is covered with the PFPE chain represented by R$^3$ in Formula (1), and frictional force between the magnetic head and the protective layer is reduced. In addition, in the lubricating layer formed using the lubricant including the fluorine-containing ether compound of the present embodiment, excellent wear resistance can be obtained by an intramolecular interaction between the end groups represented by R$^1$ and R$^5$ and one or more hydroxyl groups of at least one of R$^2$ and R$^4$, and/or an interaction between the end groups represented by R$^1$ and R$^5$ and the protective layer.

In addition, in the fluorine-containing ether compound of the present embodiment, the PFPE chain is closely attached on the protective layer by bonding between one or more hydroxyl groups of at least one of R$^2$ and R$^4$ linked to the PFPE chain, and the protective layer. Therefore, according to the fluorine-containing ether compound of the present embodiment, the lubricating layer and the protective layer are firmly bonded, and a lubricating layer having excellent wear resistance can be obtained.

[Lubricant for Magnetic Recording Medium]

The lubricant for magnetic recording media of the present embodiment includes the fluorine-containing ether compound represented by Formula (1).

The lubricant of the present embodiment can be used by being mixed with a known material used as a lubricant material as needed, within a range not impairing the characteristics obtained by including the fluorine-containing ether compound represented by Formula (1).

Specific examples of the known material include FOMBLIN (registered trademark) ZDIAC, FOMBLIN ZDEAL, and FOMBLIN AM-2001 (all manufactured by Solvey Solexis), and Moresco A20H (manufactured by Moresco). The number-average molecular weight of the known material used by being mixed with the lubricant of the present embodiment is preferably 1000 to 10000.

In a case where the lubricant of the present embodiment includes other materials in addition to the fluorine-containing ether compound represented by Formula (1), the content of the fluorine-containing ether compound represented by Formula (1) in the lubricant of the present embodiment is preferably 50% by mass or more, and more preferably 70% by mass or more. A upper limit can be optionally selected. For example, the upper limit may be 99% by mass or less, 95% by mass or less, 90% by mass or less, or 85% by mass or less.

Since the lubricant of the present embodiment includes the fluorine-containing ether compound represented by Formula (1), even when the thickness is reduced, the surface of the protective layer can be covered with high coverage, and it is possible to form a lubricating layer with excellent adhesion to the protective layer. Therefore, according to the lubricant of the present embodiment, the lubricating layer having excellent wear resistance can be obtained, even when the thickness is reduced.

In addition, since the lubricant of the present embodiment includes the fluorine-containing ether compound represented by Formula (1), the fluorine-containing ether compound in the lubricant layer not adhering (adsorbing) to the protective layer is less likely to aggregate. Accordingly, it is possible to prevent the fluorine-containing ether compound from aggregating and adhering to a magnetic head as a foreign substance (smear), and pickup is suppressed.

In addition, since the lubricant of the present embodiment includes the fluorine-containing ether compound represented by Formula (1), a lubricating layer having excellent wear resistance can be obtained by an intramolecular interaction between the end groups represented by $R^1$ and $R^5$ in Formula (1) and one or more hydroxyl groups of at least one of $R^2$ and $R^4$, and/or an interaction between the end groups and the protective layer.

[Magnetic Recording Medium]

The magnetic recording medium of the present embodiment is obtained by providing at least a magnetic layer, a protective layer, and a lubricating layer in this order on a substrate.

In the magnetic recording medium of the present embodiment, one or more base layers can be provided between the substrate and the magnetic layer, as needed. In addition, an adhesion layer and/or a soft magnetic layer can be provided between the base layer and the substrate.

FIG. 1 is a schematic sectional view showing an embodiment of the magnetic recording medium according to the present invention.

A magnetic recording medium 10 of the present embodiment has a structure in which an adhesion layer 12, a soft magnetic layer 13, a first base layer 14, a second base layer 15, a magnetic layer 16, a protective layer 17, and a lubricating layer 18 are provided in this order on a substrate 11.

"Substrate"

The substrate 11 can be optionally selected. For example, a nonmagnetic substrate or the like in which a film made of NiP or an NiP alloy is formed on a base substrate made of metal or alloy material such as Al or an Al alloy can be preferably used as a base material 11.

In addition, a nonmagnetic substrate made of a nonmetallic material such as glass, ceramics, silicon, silicon carbide, carbon, or resin may be used as the substrate 11, and a nonmagnetic substrate in which a film made of NiP or an NiP alloy is formed on a base substrate made of the nonmetallic materials may also be used as the substrate 11.

"Adhesion Layer"

The adhesion layer 12 prevents corrosion of the substrate 11 from progressing, which occurs in a case where the substrate 11 and the soft magnetic layer 13, which is provided on the adhesion layer 12, are disposed so that they are in contact with each other.

Material used for the adhesion layer 12 can be optionally selected. For example, the material can be appropriately selected from, Cr, a Cr alloy, Ti, a Ti alloy, CrTi, NiAl, an AlRu alloy, and the like. The adhesion layer 12 can be formed, for example, by a sputtering method.

"Soft Magnetic Layer"

The soft magnetic layer 13 can be optionally selected, and the soft magnetic layer 13 preferably has a structure in which a first soft magnetic film, an intermediate layer which is a Ru film, and a second soft magnetic film are laminated in this order. That is, the soft magnetic layer 13 preferably has a structure in which the intermediate layer which is the Ru film is sandwiched between the two soft magnetic films to couple the soft magnetic films above and below the intermediate layer by anti-ferro coupling (AFC).

Examples of materials of the first soft magnetic film and the second soft magnetic film include a CoZrTa alloy and a CoFe alloy.

It is preferable to add any one of Zr, Ta, and Nb to the CoFe alloy used for the first soft magnetic film and the second soft magnetic film. As the result, amorphization of the first soft magnetic film and the second soft magnetic film is promoted, an orientation of the first base layer (seed layer) can be improved, and flying height of a magnetic head can be reduced.

The soft magnetic layer 13 can be formed, for example, by a sputtering method.

"First Base Layer"

The first base layer 14 is a layer for controlling the orientation and crystal size of the second base layer 15 and the magnetic layer 16 which are provided thereon.

Examples of the first base layer 14 include a Cr layer, a Ta layer, a Ru layer, or an alloy layer of CrMo, CoW, CrW, CrV, or CrTi.

The first base layer 14 can be formed, for example, by a sputtering method.

"Second Base Layer"

The second base layer 15 is a layer that controls the orientation of the magnetic layer 16 to be favorable. The second base layer 15 can be optionally selected, and the second base layer 15 is preferably a layer including Ru or a Ru alloy.

The second base layer 15 may be a layer formed of a single layer or may be formed of a plurality of layers. In a case where the second base layer 15 is formed of a plurality of layers, all the layers may be formed of the same material, or at least one layer may be formed of a different material.

The second base layer 15 can be formed, for example, by a sputtering method.

"Magnetic Layer"

The magnetic layer 16 is formed of a magnetic film in which an easy axis of magnetization is oriented in a direction perpendicular or horizontal to a substrate surface. The magnetic layer 16 can be optionally selected, and the magnetic layer 16 is preferably a layer including Co and Pt, and, may be a layer including an oxide, Cr, B, Cu, Ta, Zr, or the like in order to further improve an SNR characteristic.

Examples of the oxide included in the magnetic layer 16 include $SiO_2$, SiO, $Cr_2O_3$, CoO, $Ta_2O_3$, and $TiO_2$.

The magnetic layer 16 may be a layer formed of a single layer or may be formed of a plurality of magnetic layers formed of materials having a different composition.

For example, in a case where the magnetic layer 16 is formed of three layers of a first magnetic layer, a second magnetic layer, and a third magnetic layer, which are laminated in this order from the bottom, the first magnetic layer preferably has a granular structure that includes a material containing Co, Cr, and Pt, and further contains an oxide. As the oxide included in the first magnetic layer, for example, oxides of Cr, Si, Ta, Al, Ti, Mg, Co, and the like are preferably used. Among these, in particular, $TiO_2$, $Cr_2O_3$, $SiO_2$, and the like can be suitably used. In addition, it is preferable that the first magnetic layer include a complex oxide obtained by adding two or more kinds of oxides. Among these, in particular, $Cr_2O_3$—$SiO_2$, $Cr_2O_3$—$TiO_2$, and $SiO_2$—$TiO_2$ can be suitably used.

The first magnetic layer can include one or more elements selected from B, Ta, Mo, Cu, Nd, W, Nb, Sm, Tb, Ru, and Re, in addition to Co, Cr, Pt, and an oxide.

For the second magnetic layer, the same material as that of the first magnetic layer can be used. The second magnetic layer preferably has a granular structure.

The third magnetic layer preferably has a non-granular structure including a material that includes Co, Cr, and Pt and does not include an oxide. The third magnetic layer can include one or more elements selected from B, Ta, Mo, Cu, Nd, W, Nb, Sm, Tb, Ru, Re, and Mn, in addition to Co, Cr, and Pt.

In a case where the magnetic layer 16 is formed of a plurality of magnetic layers, it is preferable to provide a non-magnetic layer between adjacent magnetic layers.

In a case where the magnetic layer 16 is formed of three layers that are the first magnetic layer, the second magnetic layer, and the third magnetic layer, a nonmagnetic layer is preferably provided between the first magnetic layer and the second magnetic layer and between the second magnetic layer and the third magnetic layer.

For the nonmagnetic layer provided between the adjacent magnetic layers of the magnetic layer 16, for example, Ru, a Ru alloy, a CoCr alloy, and CoCrX1 alloy (X1 represents one or more elements selected from Pt, Ta, Zr, Re, Ru, Cu, Nb, Ni, Mn, Ge, Si, O, N, W, Mo, Ti, V, and B) can be suitably used.

For the nonmagnetic layer provided between the adjacent magnetic layers of the magnetic layer 16, it is preferable to use an alloy material including an oxide, a metal nitride, or a metal carbide. Specifically, as the oxide, for example, $SiO_2$, $Al_2O_3$, $Ta_2O_5$, $Cr_2O_3$, MgO, $Y_2O_3$, and $TiO_2$ can be used. As the metal nitride, for example, AlN, $Si_3N_4$, TaN, and CrN can be used. As the metal carbide, for example, TaC, BC, and SiC can be used.

The nonmagnetic layer can be formed, for example, by a sputtering method.

In order to realize higher recording density, the magnetic layer 16 is preferably a magnetic layer for perpendicular magnetic recording in which the easy axis of magnetization is perpendicular to the substrate surface. The magnetic layer 16 may also be a magnetic layer for in-plane magnetic recording.

The magnetic layer 16 may be formed by a vapor deposition method, an ion beam sputtering method, a magnetron sputtering method, and any known method of the related art. The magnetic layer 16 is usually formed by the sputtering method.

"Protective Layer"

The protective layer 17 protects the magnetic layer 16. The protective layer 17 may be a layer formed of a single layer or may be formed of a plurality of layers. Examples of the material for the protective layer 17 include carbon, nitrogen-containing carbon, and silicon carbide.

As the protective layer 17, a carbon-based protective layer can be preferably used, and an amorphous carbon protective layer is particularly preferable. It is preferable that the protective layer 17 be the carbon-based protective layer, from the viewpoint that the interaction with the polar group (particularly, a hydroxyl group) included in the fluorine-containing ether compound in the lubricating layer 18 is further enhanced.

The adhesion force between the carbon-based protective layer and the lubricating layer 18 can be controlled by using hydrogenated carbon and/or nitrogenated carbon as the carbon-based protective layer and adjusting a hydrogen content and/or a nitrogen content in the carbon-based protective layer. The hydrogen content in the carbon-based protective layer is preferably 3 to 20 atomic % as measured by hydrogen forward scattering (HFS). In addition, the nitrogen content in the carbon-based protective layer is preferably 4 to 15 atomic % as measured by X-ray photoelectron spectroscopy (XPS).

Hydrogen and/or nitrogen included in the carbon-based protective layer need not be uniformly contained throughout the carbon-based protective layer. The carbon-based protective layer is preferably, for example, a composition gradient layer in which the nitrogen is contained on the lubricating layer 18 side of the protective layer 17 and the hydrogen is contained on the magnetic layer 16 side of the protective layer 17. In this case, the adhesion force between the magnetic layer 16 and the carbon-based protective layer and between the lubricating layer 18 and the carbon-based protective layer is further enhanced.

A film thickness of the protective layer 17 is preferably 1 nm to 7 nm. When the film thickness of the protective layer 17 is 1 nm or more, performance of the protective layer 17 is sufficiently obtained. It is preferable that the film thickness of the protective layer 17 be 7 nm or less, from the viewpoint of thinning the protective layer 17.

As the film forming method of the protective layer 17, a sputtering method using a target material containing carbon, a chemical vapor deposition (CVD) method using a hydrocarbon raw material such as ethylene or toluene, an ion beam deposition (IBD) method, or the like can be used.

In a case of forming the carbon-based protective layer as the protective layer 17, a film can be formed for example, by a DC magnetron sputtering method. In particular, in a case of forming the carbon-based protective layer as the protective layer 17, it is preferable to form an amorphous carbon protective layer by a plasma CVD method. The amorphous carbon protective layer formed by the plasma CVD method has a uniform surface and low roughness.

"Lubricating Layer"

The lubricating layer 18 prevents the magnetic recording medium 10 from being contaminated. In addition, the lubricating layer 18 reduces frictional force of a magnetic head of a magnetic recording and reproducing apparatus sliding on the magnetic recording medium 10, and improves durability of the magnetic recording medium 10.

As shown in FIG. 1, the lubricating layer 18 is preferably formed on and in contact with the protective layer 17. The lubricating layer 18 includes the fluorine-containing ether compound described above.

In a case where the protective layer 17 disposed under the lubricating layer 18 is the carbon-based protective layer, in particular, the lubricating layer 18 is bonded to the protective layer 17 with high bonding strength. As a result, even when the thickness of the lubricating layer 18 is reduced, the magnetic recording medium 10 in which the surface of the protective layer 17 is covered with high coverage is easily obtained, and it is possible to effectively prevent the surface of the magnetic recording medium 10 from being contaminated.

An average film thickness of the lubricating layer 18 can be optionally selected, and the average film thickness is preferably 0.5 nm (5 Å) to 2 nm (20 Å), and more preferably 0.5 nm (5 Å) to 1 nm (10 Å). When the average film thickness of the lubricating layer 18 is 0.5 nm or more, the lubricating layer 18 is formed in a uniform film thickness without being in an island form or a mesh form. Therefore, the surface of the protective layer 17 can be covered with high coverage by the lubricating layer 18. In addition, when setting the average film thickness of the lubricating layer 18 to 2 nm or less, the lubricating layer 18 can be sufficiently thinned, and the flying height of the magnetic head can be sufficiently reduced.

In a case where the surface of the protective layer 17 is not covered with the lubricating layer 18 with sufficiently high coverage, an environmental substance adsorbed on the surface of the magnetic recording medium 10 passes through a gap in the lubricating layer 18 and enters under the lubricating layer 18. The environmental substance that enters a lower layer of the lubricating layer 18 is adsorbed and bonded with the protective layer 17 to generate a contaminant. During magnetic recording and reproducing, the contaminant (aggregation component) adheres (transfers) to a magnetic head as a smear to damage the magnetic head and/or degrade a magnetic recording and reproducing characteristic of the magnetic recording and reproducing apparatus.

Examples of the environmental substance that generates the contaminant include a siloxane compound (cyclic siloxane or linear siloxane), an ionic compound, hydrocarbon having relatively high molecular weight such as octacosane, and a plasticizer such as dioctyl phthalate. Examples of a metal ion contained in the ionic impurities include a sodium ion and a potassium ion. Examples of an inorganic ion contained in the ionic impurities include a chlorine ion, a bromine ion, a nitrate ion, a sulfate ion, and an ammonium ion. Examples of an organic ion contained in the ionic impurities include an oxalate ion and a formate ion.

"Method of Forming Lubricating Layer"

Examples of a method of forming the lubricating layer 18 include a method in which a magnetic recording medium in the middle of production, at which each layer up to the protective layer 17 is formed on the substrate 11, is prepared, and the lubricating layer-forming solution is applied onto the protective layer 17 and dried.

The lubricating layer-forming solution is obtained by dispersing and dissolving the lubricant for magnetic recording media of the embodiment described above in a solvent as needed to set a viscosity and concentration suitable for a coating method.

Examples of the solvent used for the lubricating layer-forming solution include a fluorinated solvent such as Vertrel (registered trademark) XF (trade name, manufactured by Du Pont-Mitsui Fluorochemicals Co., Ltd.).

The coating method of the lubricating layer-forming solution is not specifically limited, and examples thereof include a spin coat method, a spray method, a paper coat method, and a dip method.

In a case of using the dip method, for example, the following method can be used. First, the substrate 11 in which each layer up to the protective layer 17 is formed is immersed in the lubricating layer-forming solution contained in an immersion tank of a dip coating apparatus. Then, the substrate 11 is pulled up from the immersion tank at a predetermined speed.

According to this, the lubricating layer-forming solution is applied to the surface on the protective layer 17 of the substrate 11.

When using the dip method, the lubricating layer-forming solution can be uniformly applied to the surface of the protective layer 17, and the lubricating layer 18 can be formed on the protective layer 17 with uniform film thickness.

In the present embodiment, it is preferable to carry out heat treatment on the substrate 11 on which the lubricating layer 18 is formed. By applying the heat treatment, the adhesion between the lubricating layer 18 and the protective layer 17 improves, and the adhesion force between the lubricating layer 18 and the protective layer 17 improves.

A heat treatment temperature is preferably set to 100° C. to 180° C. When the heat treatment temperature is 100° C. or higher, an effect of improving the adhesion between the lubricating layer 18 and the protective layer 17 is sufficiently obtained. In addition, when the heat treatment temperature is set to be 180° C. or lower, it is possible to prevent the lubricating layer 18 from being thermally decomposed. Heat treatment time is preferably 10 to 120 minutes.

The magnetic recording medium 10 of the present embodiment is obtained by providing at least the magnetic layer 16, the protective layer 17, and the lubricating layer 18 in this order on the substrate 11. In the magnetic recording medium 10 of the present embodiment, the lubricating layer 18 including the fluorine-containing ether compound described above is formed on and in contact with the protective layer 17. The surface of the protective layer 17 is covered with the lubricating layer 18 with a high coverage, even when the thickness of the lubricating layer is reduced.

Accordingly, in the magnetic recording medium 10 of the present embodiment, environmental substances that generate contaminants such as ionic impurities are prevented from entering the gap in the lubricating layer 18. Therefore, the magnetic recording medium 10 of the present embodiment has few contaminants present on the surface. In addition, in the magnetic recording medium 10 of the present embodiment, the lubricating layer 18 is less likely to generate foreign substance (smear) and can suppress pickup. In addition, in the magnetic recording medium 10 of the present embodiment, the lubricating layer 18 has excellent wear resistance. Therefore, the magnetic recording medium 10 of the present embodiment has excellent reliability and durability.

EXAMPLES

Hereinafter, the present invention will be further specifically described, using Examples and Comparative Examples. The present invention is not limited to only the following Examples.

"Production of Lubricant"

Example 1

According to a method shown below, a compound represented by Formula (A) was produced.

20.0 g of a compound (number-average molecular weight of 1000 and molecular weight distribution of 1.1) represented by $HOCH_2CF_2O(CF_2CF_2O)_q(CF_2O)_rCF_2CH_2OH$ (in the formula, q represents 4.5 and r represents 4.5) and 1.97 g of a compound represented by Formula (20), and 12 mL of t-butanol were charged into a 100-mL eggplant flask under a nitrogen gas atmosphere, and stirred at room temperature to become homogeneous. 0.674 g of potassium tert-butoxide was further added to the homogeneous solution, and stirred and reacted at 70° C. for 8 hours to obtain a reaction product.

The compound represented by Formula (20) was synthesized using phenol and 2-bromoethyloxirane.

The obtained reaction product was cooled to 25° C. and neutralized with 0.5 mol/L hydrochloric acid, and then extracted using Vertrel XF (manufactured by Du Pont-Mitsui Fluorochemicals Co., Ltd.) (hereinafter, Vertrel XF), and the organic layer was washed with water. This was dehydrated with anhydrous sodium sulfate. The desiccant was filtered off, and then the filtrate was concentrated. The residue was purified by silica gel column chromatography to obtain 9.31 g of a compound represented by Formula (21).

(20)

(21)

(In Formula (21), m represents 4.5 and n represents 4.5.)

5.81 g of the compound represented by Formula (21), 1.90 g of the compound represented by Formula (22), and 50 mL of t-butanol were charged into a 200-mL eggplant flask under a nitrogen gas atmosphere, and stirred at room temperature to become homogeneous. 0.168 g of potassium tert-butoxide was added to the homogeneous solution, and stirred at 70° C. for 16 hours to react.

(22)

A solution after the reaction was finished was returned to room temperature, and 20 g of 10% hydrogen chloride-methanol solution was added thereto and stirred at room temperature for 1 hour. The reaction solution was transferred to a beaker containing 70 mL of 8% aqueous sodium bicarbonate, and extracted twice with 200 mL of ethyl acetate. The organic layer was washed with water and dehydrated with anhydrous sodium sulfate.

The desiccant was filtered off, and then the filtrate was concentrated. The residue was purified by silica gel column chromatography to obtain 3.71 g of Compound (A). In Formula (A), m is 4.5 and n is 4.5.

$^1$H-NMR measurement of the obtained Compound (A) was conducted, and a structure was identified from the following results.

Compound (A); $^1$H-NMR(CD$_3$COCD$_3$);

δ [ppm] 1.6 to 1.8 (2H), 3.6 to 4.2 (14H), 6.9 (5H)

Example 2

3.75 g of Compound (B) was obtained by performing the same operation as in Example 1, except that 1.03 g of a compound represented by Formula (23) was used instead of the compound represented by Formula (22). In Formula (B), m is 4.5 and n is 4.5.

The compound represented by Formula (23) was synthesized by protecting the hydroxyl group of 3-buten-1-ol with dihydropyran and oxidizing the double bond.

(23)

$^1$H-NMR measurement of the obtained Compound (B) was conducted, and a structure was identified from the following results.

Compound (B); $^1$H-NMR(CD$_3$COCD$_3$);

δ [ppm] 1.6 to 1.8 (2H), 3.6 to 4.2 (16H), 6.9 (5H)

Example 3

3.84 g of Compound (C) was obtained by performing the same operation as in Example 1, except that 1.21 g of a compound represented by Formula (24) was used instead of the compound represented by Formula (22). In Formula (C), m is 4.5 and n is 4.5.

The compound represented by Formula (24) was synthesized by protecting the hydroxyl group of ethylene glycol monoallyl ether with dihydropyran and then oxidizing the double bond.

(24)

$^1$H-NMR measurement of the obtained Compound (C) was conducted, and a structure was identified from the following results.

Compound (C); $^1$H-NMR (CD$_3$COCD$_3$);

δ [ppm] 1.6 to 1.8 (2H), 3.6 to 4.2 (18H), 6.9 (5H)

Example 4

3.56 g of Compound (D) was obtained by way of an intermediate represented by Formula (26), by performing the same operation as in Example 1 except that 1.53 g of a compound represented by Formula (25) was used instead of the compound represented by Formula (20). In Formula (D), m is 4.5 and n is 4.5.

The compound represented by Formula (25) was synthesized using allyl alcohol and 2-bromoethyloxirane.

(25)

(26)

(In Formula (26), m represents 4.5 and n represents 4.5.)

$^1$H-NMR measurement of the obtained Compound (D) was conducted, and a structure was identified from the following results.

Compound (D); $^1$H-NMR (CD$_3$COCD$_3$):

δ [ppm] 1.6 to 1.8 (2H), 3.5 to 4.2 (16H), 5.1 to 5.3 (2H), 5.9 (1H)

Example 5

3.60 g of Compound (E) was obtained by performing the same operation as in Example 2, except that a compound represented by Formula (26) was used instead of the compound represented by Formula (21). In Formula (E), m is 4.5 and n is 4.5.

$^1$H-NMR measurement of the obtained Compound (E) was conducted, and a structure was identified from the following results.

Compound (E); $^1$H-NMR (CD$_3$COCD$_3$);

δ [ppm] 1.6 to 1.8 (2H), 3.5 to 4.2 (18H), 5.1 to 5.3 (2H), 5.9 (1H)

Example 6

3.69 g of Compound (F) was obtained by performing the same operation as in Example 3, except that a compound represented by Formula (26) was used instead of the compound represented by Formula (21). In Formula (F), m is 4.5 and n is 4.5.

$^1$H-NMR measurement of the obtained Compound (F) was conducted, and a structure was identified from the following results.

Compound (F); $^1$H-NMR (CD$_3$COCD$_3$);

δ [ppm] 1.6 to 1.8 (2H), 3.5 to 4.2 (20H), 5.1 to 5.3 (2H), 5.9 (1H)

Example 7

3.77 g of Compound (G) was obtained by way of an intermediate represented by Formula (28), by performing the same operation as in Example 1 except that 2.21 g of a compound represented by Formula (27) was used instead of the compound represented by Formula (20). In Formula (G), m is 4.5 and n is 4.5.

The compound represented by Formula (27) was synthesized using thiophene ethanol and 2-bromoethyloxirane.

$^1$H-NMR measurement of the obtained Compound (G) was conducted, and a structure was identified from the following results.

Compound (G); $^1$H-NMR (CD$_3$COCD$_3$);

δ [ppm] 1.6 to 1.8 (2H), 3.1 (2H), 3.5 to 4.2 (16H), 6.8 to 7.0 (2H), 7.2 (1H)

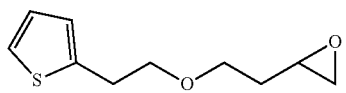

(27)

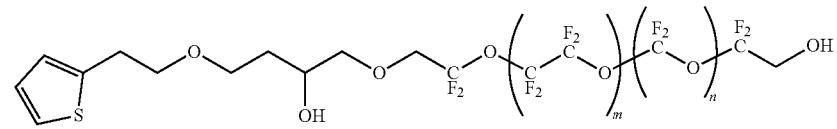

(28)

(In Formula (28), m represents 4.5 and n represents 4.5.)

Example 8

3.81 g of Compound (H) was obtained by performing the same operation as in Example 2, except that a compound represented by Formula (28) was used instead of the compound represented by Formula (21). In Formula (H), m is 4.5 and n is 4.5.

$^1$H-NMR measurement of the obtained Compound (H) was conducted, and a structure was identified from the following results.

Compound (H); $^1$H-NMR (CD$_3$COCD$_3$);

δ [ppm] 1.6 to 1.8 (2H), 3.1 (2H), 3.5 to 4.2 (18H), 6.8 to 7.0 (2H), 7.2 (1H)

Example 9

3.90 g of Compound (I) was obtained by performing the same operation as in Example 3, except that a compound represented by Formula (28) was used instead of the compound represented by Formula (21). In Formula (I), m is 4.5 and n is 4.5.

$^1$H-NMR measurement of the obtained Compound (I) was conducted, and a structure was identified from the following results.

Compound (I); $^1$H-NMR (CD$_3$COCD$_3$);

δ [ppm] 1.6 to 1.8 (2H), 3.1 (2H), 3.5 to 4.2 (20H), 6.8 to 7.0 (2H), 7.2 (1H)

Example 10

3.90 g of Compound (J) was obtained by performing the same operation as in Example 6, except that 1.30 g of a compound represented by Formula (29) was used instead of the compound represented by Formula (24). In Formula (J), m is 4.5 and n is 4.5.

The compound represented by Formula (29) was synthesized by reacting a compound, in which a hydroxyl group on one side of ethylene glycol was protected with dihydropyran, with 2-bromoethyloxirane.

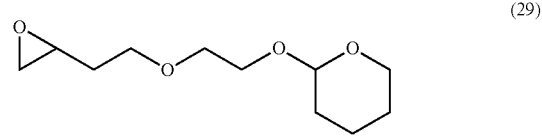 [SMILES: C1CCC(OCCOCCC2CO2)OC1]

(29)

$^1$H-NMR measurement of the obtained Compound (J) was conducted, and a structure was identified from the following results.

Compound (J); $^1$H-NMR (CD$_3$COCD$_3$);

δ [ppm] 1.6 to 1.8 (4H), 3.1 (2H), 3.5 to 4.2 (20H), 5.1 to 5.3 (2H), 5.9 (1H)

Example 11

3.99 g of Compound (K) was obtained by performing the same operation as in Example 3, except that a compound represented by Formula (30) was used instead of the compound represented by Formula (20). In Formula (K), m is 4.5 and n is 4.5.

The compound represented by Formula (30) was synthesized by oxidizing a double bond group on one side of the reaction product of 3-buten-1-ol and epichlorohydrin.

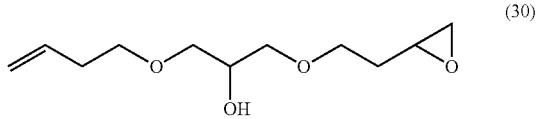

(30)

¹H-NMR measurement of the obtained Compound (K) was conducted, and a structure was identified from the following results.

Compound (K); ¹H-NMR (CD$_3$COCD$_3$);

δ [ppm] 1.6 to 1.8 (2H), 2.4 (2H), 3.5 to 4.2 (25H), 5.1 to 5.3 (2H), 5.9 (1H)

Example 12

5.0 g of a compound (number-average molecular weight of 1000 and molecular weight distribution of 1.1) represented by HOCH$_2$CF$_2$O(CF$_2$CF$_2$O)$_q$(CF$_2$O)$_r$CF$_2$CH$_2$OH (in the formula, q represents 4.5 and r represents 4.5) and 2.16 g of a compound represented by Formula (30), and 10 mL of t-butanol were charged into a 100-mL eggplant flask under a nitrogen gas atmosphere, and stirred at room temperature to become homogeneous. 0.337 g of potassium tert-butoxide was further added to the homogeneous solution, and stirred at 70° C. for 12 hours to react.

The reaction solution was returned to room temperature, and 40 mL of water was added thereto. Extraction was performed twice with 80 mL of ethyl acetate. The organic layer was washed with water and dehydrated with anhydrous sodium sulfate. The desiccant was filtered off, and then the filtrate was concentrated. The residue was purified by silica gel column chromatography to obtain 4.29 g of Compound (L). In Formula (L), m is 4.5 and n is 4.5.

¹H-NMR measurement of the obtained Compound (L) was conducted, and a structure was identified from the following results.

Compound (L); ¹H-NMR (CD$_3$COCD$_3$);

δ [ppm] 1.6 to 1.8 (4H), 2.4 (4H), 3.5 to 4.2 (28H), 5.1 to 5.3 (4H), 5.9 (2H)

Example 13

3.81 g of Compound (M) was obtained by performing the same operation as in Example (10), except that 20 g of a compound (number-average molecular weight of 1000 and molecular weight distribution of 1.1) represented by HOCH$_2$CF$_2$CF$_2$O(CF$_2$CF$_2$CF$_2$O)$_s$CF$_2$CF$_2$CH$_2$OH (in the formula, s represents 4.5) was used instead of the compound (number-average molecular weight of 1000 and molecular weight distribution of 1.1) represented by HOCH$_2$CF$_2$O(CF$_2$CF$_2$O)$_q$(CF$_2$O)$_r$CF$_2$CH$_2$OH (in the formula, q is 4.5 and r is 4.5). In Formula (M), z is 4.5.

¹H-NMR measurement of the obtained Compound (M) was conducted, and a structure was identified from the following results.

Compound (M); ¹H-NMR (CD$_3$COCD$_3$);

δ [ppm] 1.6 to 1.8 (4H), 3.5 to 4.2 (20H), 5.1 to 5.3 (2H), 5.9 (1H)

Example 14

3.98 g of Compound (N) was obtained by performing the same operation as in Example (12), except that 1.64 g of a compound represented by Formula (20) was used instead of the compound represented by Formula (30).

In Formula (N), m is 4.5 and n is 4.5.

¹H-NMR measurement of the obtained Compound (N) was conducted, and a structure was identified from the following results.

Compound (N); ¹H-NMR (CD$_3$COCD$_3$);

δ [ppm] 1.6 to 1.8 (4H), 3.6 to 4.2 (14H), 6.9 (10H)

Example 15

3.78 g of Compound (O) was obtained by performing the same operation as in Example (12), except that 2.16 g of a compound represented by Formula (29) was used instead of the compound represented by Formula (30).

In Formula (O), m is 4.5 and n is 4.5.

¹H-NMR measurement of the obtained Compound (O) was conducted, and a structure was identified from the following results.

Compound (O); ¹H-NMR (CD$_3$COCD$_3$);

δ [ppm] 1.6 to 1.8 (4H), 3.6 to 4.2 (22H)

Example 16

4.06 g of Compound (P) was obtained by performing the same operation as in Example (11), except that 0.76 g of a compound represented by Formula (31) was used instead of the compound represented by Formula (24).

In Formula (P), m is 4.5 and n is 4.5.

The compound represented by Formula (31) was synthesized by oxidizing a reaction product of ethylene cyanohydrin and allyl bromide.

(31)

1H-NMR measurement of the obtained Compound (P) was conducted, and a structure was identified from the following results.

Compound (P); 1H-NMR (CD$_3$COCD$_3$);

δ [ppm] 1.6 to 1.8 (2H), 2.4 (2H), 3.5 to 4.2 (25H), 5.1 to 5.3 (2H), 5.9 (1H)

Example 17

3.80 g of Compound (Q) was obtained by performing the same operation as in Example 10, except that 0.85 g of a compound represented by Formula (32) was used instead of the compound represented by Formula (29). In Formula (Q), m is 4.5 and n is 4.5.

The compound represented by Formula (32) was synthesized by oxidizing the reaction product of ethylene cyanohydrin and 4-bromo-1-butene.

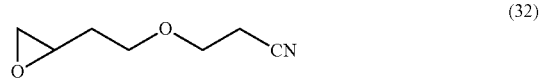

(32)

$^1$H-NMR measurement of the obtained Compound (Q) was conducted, and a structure was identified from the following results.

Compound (Q); $^1$H-NMR (CD$_3$COCD$_3$);

δ [ppm] 1.6 to 1.8 (4H), 3.1 (2H), 3.5 to 4.2 (20H), 5.1 to 5.3 (2H), 5.9 (1H)

Example 18

3.62 g of Compound (R) was obtained by performing the same operation as in Example 11, except that 20.5 g of a compound represented by Formula (9) was used instead of the compound represented by Formula (8). In Formula (R), m is 4.5.

$^1$H-NMR measurement of the obtained Compound (R) was conducted, and a structure was identified from the following results.

Compound (R); $^1$H-NMR (CD$_3$COCD$_3$);

δ [ppm] 1.6 to 1.8 (2H), 2.4 (2H), 3.5 to 4.2 (25H), 5.1 to 5.3 (2H), 5.9 (1H)

Example 19

3.55 g of Compound (S) was obtained by performing the same operation as in Example 11, except that a compound represented by Formula (33) was used instead of the compound represented by Formula (24). In Formula (S), m is 4.5 and n is 4.5.

The compound represented by Formula (33) was obtained from epibromohydrin and a compound, wherein the compound is obtained such that after a reaction product of ethylene glycol mono tert-butyl ether and epibromohydrin was hydrolyzed, the primary hydroxyl group was protected with a tert-butyldimethylsilyl group and then the secondary hydroxyl group was protected with a tetrahydropyran group, and the tert-butyldimethylsilyl group was deprotected.

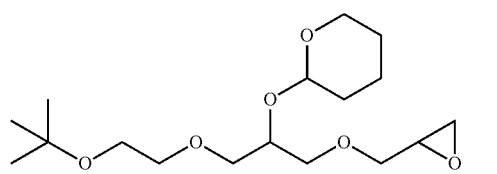

(33)

$^1$H-NMR measurement of the obtained Compound (S) was conducted, and a structure was identified from the following results.

Compound (S); $^1$H-NMR (CD$_3$COCD$_3$);

δ [ppm] 1.6 to 1.8 (2H), 2.4 (2H), 3.5 to 4.2 (30H), 5.1 to 5.3 (2H), 5.9 (1H)

Example 20

3.65 g of Compound (T) was obtained by performing the same operation as in Example 11, except that a compound represented by Formula (34) was used instead of the compound represented by Formula (24). In Formula (T), m is 4.5 and n is 4.5.

The compound represented by Formula (34) was obtained from epibromohydrin and a compound, wherein the compound is obtained such that after a reaction product of cyanopropanol and epibromohydrin was hydrolyzed, the primary hydroxyl group was protected with a tert-butyldimethylsilyl group and then the secondary hydroxyl group was protected with a tetrahydropyran group, and the tert-butyldimethylsilyl group was deprotected.

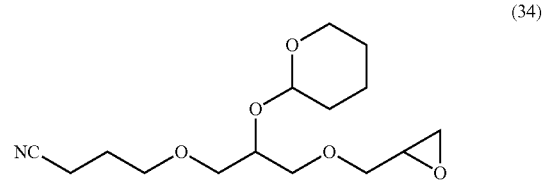 [SMILES: N#CCCCOCC(COCC1CO1)OC1CCCCO1]

(34)

$^1$H-NMR measurement of the obtained Compound (T) was conducted, and a structure was identified from the following results.

Compound (T); $^1$H-NMR (CD$_3$COCD$_3$);

δ [ppm] 1.6 to 1.8 (2H), 2.2 to 2.4 (4H), 2.7 (2H), 3.5 to 4.2 (28H), 5.1 to 5.3 (2H), 5.9 (1H)

Comparative Example 1

A compound represented by Formula (X) was synthesized by the method described in Patent Document 3.

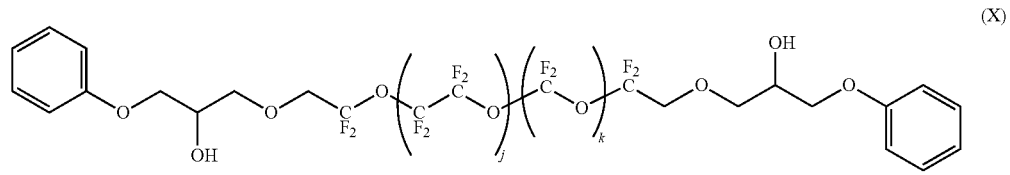

(X)

(In Formula (X), j represents 4.5 and k represents 4.5.)

Comparative Example 2

A compound represented by Formula (Y) was synthesized by the method described in Patent Document 1.

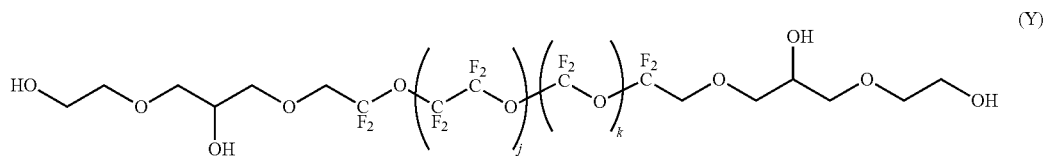

(Y)

(In Formula (Y), j represents 4.5 and k represents 4.5.)

Comparative Example 3

A compound represented by Formula (Z) was synthesized by the method described in Patent Document 2.

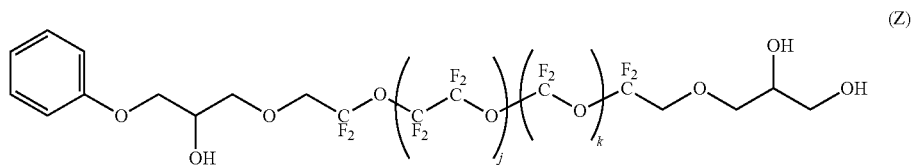

(Z)

(In Formula (Z), j represents 4.5 and k represents 4.5.)

Tables 1 and 2 show the structures of $R^1$ to $R^5$ when the compounds of Examples 1 to 20 and Comparative Examples 1 to 3 obtained as above were applied to Formula (1). The number-average molecular weights (Mn) of the compounds of Examples 1 to 20 and Comparative Examples 1 to 3 were determined by the $^1$H-NMR and $^{19}$F-NMR measurements described above. The results thereof are shown in Tables 1 and 2.

TABLE 1

| Example | $R^1$ | $R^2$ | $R^3$ | $R^4$ | $R^5$ | Mn |
|---|---|---|---|---|---|---|
| 1 | phenyl | Formula (2) a = 0 b = 1 c = 2 | Formula (8) m = 4.5 n = 4.5 | Formula (3) d = 0 e = 0 f = 1 | —H | 1235 |
| 2 | phenyl | Formula (2) a = 0 b = 1 c = 2 | Formula (8) m = 4.5 n = 4.5 | Formula (3) d = 1 e = 2 f = 0 | —H | 1249 |
| 3 | phenyl | Formula (2) a = 0 b = 1 c = 2 | Formula (8) m = 4.5 n = 4.5 | Formula (3) d = 0 e = 0 f = 1 | —CH$_2$CH$_2$OH | 1279 |
| 4 | allyl | Formula (2) a = 0 b = 1 c = 2 | Formula (8) m = 4.5 n = 4.5 | Formula (3) d = 0 e = 0 f = 1 | —H | 1185 |
| 5 | allyl | Formula (2) a = 0 b = 1 c = 2 | Formula (8) m = 4.5 n = 4.5 | Formula (3) d = 1 e = 2 f = 0 | —H | 1199 |
| 6 | allyl | Formula (2) a = 0 b = 1 c = 2 | Formula(8) m = 4.5 n = 4.5 | Formula (3) d = 0 e = 0 f = 1 | —CH$_2$CH$_2$OH | 1229 |
| 7 | thienylethyl | Formula (2) a = 0 b = 1 c = 2 | Formula (8) m = 4.5 n = 4.5 | Formula (3) d = 0 e = 0 f = 1 | —H | 1255 |

TABLE 1-continued

| Example | R¹ | R² | R³ | R⁴ | R⁵ | Mn |
|---|---|---|---|---|---|---|
| 8 | 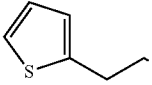 a = 0, b = 1, c = 2 | Formula (2) | Formula (8) m = 4.5 n = 4.5 | Formula (3) d = 1 e = 2 f = 0 | —H | 1269 |
| 9 | 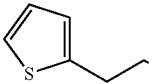 a = 0, b = 1, c = 2 | Formula (2) | Formula (8) m = 4.5 n = 4.5 | Formula (3) d = 0 e = 0 f = 1 | —CH₂CH₂OH | 1299 |

TABLE 2

| Example | R¹ | R² | R³ | R⁴ | R⁵ | M |
|---|---|---|---|---|---|---|
| 10 | 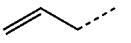 a = 0, b = 1, c = 2 | Formula (2) | Formula (8) m = 4.5 n = 4.5 | Formula (3) d = 1 e = 2 f = 0 | —CH₂CH₂OH | 1299 |
| 11 | 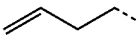 a = 1, b = 1, c = 2 | Formula (2) | Formula (8) m = 4.5 n = 4.5 | Formula (3) d = 0 e = 0 f = 1 | —CH₂CH₂OH | 1311 |
| 12 | 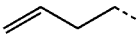 a = 1, b = 1, c = 2 | Formula (2) | Formula (8) m = 4.5 n = 4.5 | Formula (3) d = 1 e = 2 f = 1 | 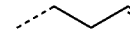 | 1429 |
| 13 | 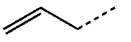 a = 0, b = 1, c = 2 | Formula (2) | Formula (10) z = 4.5 | Formula (3) d = 1 e = 2 f = 0 | —CH₂CH₂OH | 1271 |
| 14 | 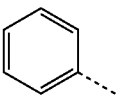 a = 0, b = 1, c = 2 | Formula (2) | Formula (8) m = 4.5 n = 4.5 | Formula (3) d = 1 e = 2 f = 0 | 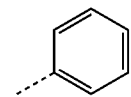 | 1325 |
| 15 | HOCH₂CH₂— | Formula (2) a = 0, b = 1, c = 2 | Formula (8) m = 4.5 n = 4.5 | Formula (3) d = 1 e = 2 f = 0 | —CH₂CH₂OH | 1261 |
| 16 | 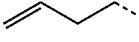 a = 1, b = 1, c = 2 | Formula (2) | Formula (8) m = 4.5 n = 4.5 | Formula (3) d = 0 e = 0 f = 1 | —CH₂CH₂CN | 1340 |
| 17 | 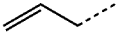 a = 0, b = 1, c = 2 | Formula (2) | Formula (8) m = 4.5 n = 4.5 | Formula (3) d = 1 e = 2 f = 0 | —CH₂CH₂CN | 1266 |
| 18 | 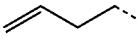 a = 1, b = 1, c = 2 | Formula (2) | Formula (9) y = 4.5 | Formula (3) d = 0 e = 0 f = 1 | —CH₂CH₂OH | 1361 |
| 19 | 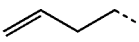 a = 1, b = 1, c = 2 | Formula (2) | Formula (8) m = 4.5 n = 4.5 | Formula (3) d = 0 e = 0 f = 2 | —CH₂CH₂OH | 1369 |
| 20 | 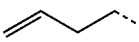 a = 1, b = 1, c = 2 | Formula (2) | Formula (8) m = 4.5 n = 4.5 | Formula (3) d = 0 e = 0 f = 2 | —CH₂CH₂CH₂CN | 1392 |

Next, a lubricating layer-forming solution was prepared using the compounds obtained in Examples 1 to 20 and Comparative Examples 1 to 3 by the method shown below. Then, according to the method shown below, the lubricating layer of the magnetic recording medium was formed using the obtained lubricating layer-forming solution, and the magnetic recording media of Examples 1 to 20 and Comparative Examples 1 to 3 were obtained.

"Lubricating Layer-Forming Solution"

Each of the compounds obtained in Examples 1 to 20 and Comparative Examples 1 to 3 was dissolved in Vertrel (registered trademark) XF (trade name, manufactured by Du Pont-Mitsui Fluorochemicals Co., Ltd.) as a fluorinated solvent, and was diluted with Vertrel such that the film thickness when applied to the protective layer was 9 Å to 10 Å to obtain a lubricating layer-forming solution.

"Magnetic Recording Medium"

A magnetic recording medium, in which an adhesion layer, a soft magnetic layer, a first base layer, a second base layer, a magnetic layer, and a protective layer were provided in this order on a substrate having a diameter of 65 mm, was prepared. The protective layer was formed from carbon.

The lubricating layer-forming solutions of Examples 1 to 20 and Comparative Examples 1 to 3 were respectively applied by a dip method on the protective layer of the magnetic recording medium in which each layer up to the protective layer was formed. The dip method was performed under conditions of an immersion speed of 10 mm/sec, an immersion time of 30 sec, and a pulling speed of 1.2 mm/sec.

Thereafter, the magnetic recording medium coated with the lubricating layer-forming solution was placed in a thermostatic chamber at 120° C. and heated for 10 minutes to remove the solvent in the lubricating layer-forming solution. Accordingly, the lubricating layer was formed on the protective layer to form a magnetic recording medium.

The film thickness of a lubricating layer of each of the magnetic recording media obtained in this manner in Examples 1 to 20 and Comparative Examples 1 to 3 was measured using FT-IR (trade name: Nicolet iS50, manufactured by Thermo Fisher Scientific). The results thereof are shown in Table 3.

Next, a wear resistance test shown below was conducted on the magnetic recording media of Examples 1 to 20 and Comparative Examples 1 to 3.

(Wear Resistance Test)

Using a pin-on-disk type friction and wear tester, an alumina ball having a diameter of 2 mm as a contact was slid on the lubricating layer of the magnetic recording medium, with a load of 40 gf at a sliding speed of 0.25 m/sec, to measure a coefficient of friction of a surface of the lubricating layer. Then, sliding time until the coefficient of friction of the surface of the lubricating layer sharply increased was measured. The sliding time until the coefficient of friction sharply increased was measured four times for each lubricating layer of the magnetic recording medium, and an average value (time) thereof was used as an indicator of the wear resistance of the lubricant coating film.

Table 3 shows the results of the magnetic recording media using the compounds of Examples 1 to 20 and the compounds of Comparative Examples 1 to 3. The evaluation of time until the coefficient of friction increases was as follows. The higher the time until the coefficient of friction increases, the better.

A: 650 sec or more
B: 550 sec or more and less than 650 sec
C: 450 sec or more and less than 550 sec
D: Less than 450 sec The time until the coefficient of friction sharply increases can be used as an indicator of the wear resistance of the lubricating layer for the following reason. In the lubricating layer of the magnetic recording medium, wear progresses according to use of the magnetic recording medium. When the lubricating layer disappears due to wear, the contact and the protective layer are in direct contact with each other and cause the coefficient of friction to sharply increase. The time until the coefficient of friction sharply increases is considered to have a correlation with the friction test.

TABLE 3

|  | Compound | Film thickness (Å) | Time until coefficient of friction increases (sec) |
| --- | --- | --- | --- |
| Example 1 | A | 9.5 | B |
| Example 2 | B | 9.5 | B |
| Example 3 | C | 9.5 | A |
| Example 4 | D | 9.5 | B |
| Example 5 | E | 9.5 | A |
| Example 6 | F | 9.5 | A |
| Example 7 | G | 9.5 | B |
| Example 8 | H | 9.5 | A |
| Example 9 | I | 9.5 | A |
| Example 10 | J | 9.5 | A |
| Example 11 | K | 9.5 | A |
| Example 12 | L | 9.5 | A |
| Example 13 | M | 9.5 | A |
| Example 14 | N | 9.5 | B |
| Example 15 | O | 9.5 | B |
| Example 16 | P | 9.5 | A |
| Example 17 | Q | 9.5 | B |
| Example 18 | R | 9.5 | A |
| Example 19 | S | 9.5 | A |
| Example 20 | T | 9.5 | A |
| Comparative Example 1 | X | 9.5 | D |
| Comparative Example 2 | Y | 9.5 | C |
| Comparative Example 3 | Z | 9.5 | C |

As shown in Table 3, the magnetic recording media of Examples 1 to 20 have a longer sliding time until the coefficient of friction sharply increases, and were more favorable in wear resistance, compared to the magnetic recording medium of Comparative Examples 1 to 3.

It is presumed that the aforementioned results can be achieved because, in the magnetic recording media of Examples 1 to 20, —$R^2$—$CH_2$—$R^3$ is a linking group represented by Formula (2), and $R^3$—$CH_2$—$R^4$— is a linking group represented by Formula (3) in the compound represented by Formula (1) which forms the lubricating layer. In addition, in Examples 3, 6, 9, sliding time until the coefficient of friction sharply increases was longer, and wear resistance was more favorable, compared to Examples 1, 4, 7. It is presumed that the aforementioned results can be achieved because, in the magnetic recording medium of Examples 3, 6, and 9, the distance between the hydroxyl group included in $R^4$ and the hydroxyl group included in $R^5$ in the compound represented by Formula (1) contained in the lubricating layer is long, and therefore the compound is easily arranged in a state of spreading in a surface direction on the protective layer.

INDUSTRIAL APPLICABILITY

When using the lubricant for magnetic recording media including the fluorine-containing ether compound of the present invention, it is possible to form a lubricating layer in which excellent wear resistance can be realized even when the thickness thereof is reduced.

That is, according to the present invention, it is possible to provide a fluorine-containing ether compound which can form a lubricating layer having excellent wear resistance, even when the thickness is reduced, and can be suitably used as a material of a lubricant for magnetic recording media.

REFERENCE SIGNS LIST

10 . . . Magnetic recording medium
11 . . . Substrate
12 . . . Adhesion layer
13 . . . Soft magnetic layer
14 . . . First base layer
15 . . . Second base layer
16 . . . Magnetic layer
17 . . . Protective layer
18 . . . Lubricating layer

The invention claimed is:

1. A fluorine-containing ether compound represented by Formula (1):

$$R^1-R^2-CH_2-R^3-CH_2-R^4-R^5 \quad (1)$$

(in Formula (1), $R^3$ is a perfluoropolyether chain, $R^1$ is an end group bonded to $R^2$, $R^5$ is an end group bonded to $R^4$, $R^1$ and $R^5$ are each independently any one of an alkyl group that may have a substituent, an organic group having at least one double bond or at least one triple bond, and a hydrogen atom, $-R^2-CH_2-R^3-$ is represented by Formula (2), and $R^3-CH_2-R^4-$ is represented by Formula (3))

$$-[A]-[B]-O-CH_2-R^3 \quad (2)$$

$$R^3-CH_2-O-[C]-[D]- \quad (3)$$

(in Formula (2), [A] is represented by Formula (4), [B] is represented by Formula (5), and [A] and [B] in Formula (2) may be interchanged)

(in Formula (3), [C] is represented by Formula (6), [D] is represented by Formula (7), and [C] and [D] in Formula (3) may be interchanged)

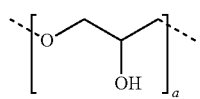

(4)

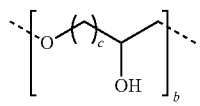

(5)

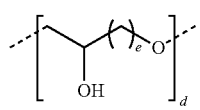

(6)

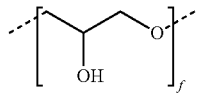

(7)

(a in Formula (4) and b in Formula (5) are integers of 0 to 2, c in Formula (5) is an integer of 2 to 5, and d in Formula (6) and f in Formula (7) are an integer of 0 to 2, e in Formula (6) is an integer of 2 to 5, and at least one of b in Formula (5) and d in Formula (6) is 1 or more).

2. The fluorine-containing ether compound according to claim 1,
wherein the alkyl group that may have a substituent is an alkyl group having 1 to 6 carbon atoms, wherein the alkyl group includes a hydroxyl group or a cyano group.

3. The fluorine-containing ether compound according to claim 1,
wherein the organic group having at least one double bond or at least one triple bond is any one of a group containing an aromatic ring, a group containing a heterocyclic ring, an alkenyl group, and an alkynyl group.

4. The fluorine-containing ether compound according to claim 1,
wherein $R^3$ in Formula (1) is represented by any one of Formulas (8) to (10), $$-CF_2O-(CF_2CF_2O)_m-(CF_2O)_n-CF_2- \quad (8)$$

(m and n in Formula (8) represent average polymerization degrees, and each represent 0 to 30, with a proviso that m or n is 0.1 or more)

$$-CF(CF_3)-(OCF(CF_3)CF_2)_y-OCF(CF_3)- \quad (9)$$

(y in Formula (9) represents an average degree of polymerization and represents 0.1 to 30)

$$-CF_2CF_2O-(CF_2CF_2CF_2O)_z-CF_2CF_2- \quad (10)$$

(in Formula (10), z represents an average degree of polymerization and represents 0.1 to 30).

5. The fluorine-containing ether compound according to claim 1,
wherein a number-average molecular weight thereof is in a range of 500 to 10000.

6. A lubricant for magnetic recording media, comprising:
the fluorine-containing ether compound according to claim 1.

7. A magnetic recording medium, comprising:
a substrate; and
at least a magnetic layer, a protective layer, and a lubricating layer in this order on the substrate,
wherein the lubricating layer includes the fluorine-containing ether compound according to claim 1.

8. The magnetic recording medium according to claim 7, wherein an average film thickness of the lubricating layer is 0.5 nm to 2 nm.

\* \* \* \* \*